US 12,295,822 B2

(12) United States Patent
Wciorka et al.

(10) Patent No.: US 12,295,822 B2
(45) Date of Patent: *May 13, 2025

(54) DISPOSABLE ABSORBENT ARTICLE

(71) Applicant: The Procter & Gamble Company, Cincinnati, OH (US)

(72) Inventors: Maja Wciorka, Braunschweig (DE); Carsten Heinrich Kreuzer, Hofheim (DE); Udo Friedel Schoenborn, Bad Soden (DE)

(73) Assignee: The Procter & Gamble Company, Cincinnati, OH (US)

( * ) Notice: Subject to any disclaimer, the term of this patent is extended or adjusted under 35 U.S.C. 154(b) by 195 days.

This patent is subject to a terminal disclaimer.

(21) Appl. No.: 17/979,829

(22) Filed: Nov. 3, 2022

(65) Prior Publication Data
US 2023/0052286 A1 Feb. 16, 2023

Related U.S. Application Data

(63) Continuation of application No. 17/318,039, filed on May 12, 2021, which is a continuation of application
(Continued)

(51) Int. Cl.
*A61F 13/539* (2006.01)
*A61F 13/495* (2006.01)
(Continued)

(52) U.S. Cl.
CPC .......... *A61F 13/539* (2013.01); *A61F 13/495* (2013.01); *A61F 13/496* (2013.01);
(Continued)

(58) Field of Classification Search
CPC ........ A61F 13/539; A61F 2013/53908–53991; A61F 13/495; A61F 2013/5315; A61F 2013/4951–4958
See application file for complete search history.

(56) References Cited

U.S. PATENT DOCUMENTS

| | | | |
|---|---|---|---|
| 3,071,138 A | 1/1963 | Gustavo | |
| 3,441,023 A | 4/1969 | Rijssenbeek | |

(Continued)

FOREIGN PATENT DOCUMENTS

| | | |
|---|---|---|
| EP | 0149880 A2 | 7/1985 |
| EP | 0203289 A2 | 12/1986 |

(Continued)

OTHER PUBLICATIONS

PCT Search Report and Written Opinion for PCT/US2009/040903 dated Jul. 29, 2009.
(Continued)

*Primary Examiner* — Susan S Su
(74) *Attorney, Agent, or Firm* — Daniel S. Albrecht

(57) ABSTRACT

A disposable absorbent article is provided having an absorbent core located in a chassis and including absorbent particulate polymer material defining at least one cavity. The absorbent core may be substantially cellulose free or comprise a combination of particulate absorbent polymer material and wood pulp. Methods for making such an absorbent core and corresponding disposable absorbent article are also disclosed.

14 Claims, 26 Drawing Sheets

Related U.S. Application Data

No. 15/952,702, filed on Apr. 13, 2018, now Pat. No. 11,083,644, which is a continuation of application No. 14/700,188, filed on Apr. 30, 2015, now Pat. No. 10,434,018, which is a continuation of application No. 12/416,383, filed on Apr. 1, 2009, now Pat. No. 9,044,359.

(60) Provisional application No. 61/048,668, filed on Apr. 29, 2008.

(51) Int. Cl.
 A61F 13/496 (2006.01)
 A61F 13/536 (2006.01)
 A61F 13/53 (2006.01)

(52) U.S. Cl.
 CPC .... *A61F 13/536* (2013.01); *A61F 2013/5307* (2013.01); *A61F 2013/53908* (2013.01)

(56) References Cited

U.S. PATENT DOCUMENTS

| | | |
|---|---|---|
| 3,670,731 A | 6/1972 | Harmon |
| 3,848,594 A | 11/1974 | Buell |
| 3,860,003 A | 1/1975 | Buell |
| 3,889,679 A | 6/1975 | Taylor |
| 3,908,659 A | 9/1975 | Wehrmeyer et al. |
| 4,027,672 A | 6/1977 | Karami |
| 4,055,180 A | 10/1977 | Karami |
| 4,259,220 A | 3/1981 | Bunnelle et al. |
| 4,381,783 A | 5/1983 | Elias |
| 4,469,710 A | 9/1984 | Rielley et al. |
| 4,515,595 A | 5/1985 | Kievit |
| 4,596,568 A | 6/1986 | Flug |
| 4,610,678 A | 9/1986 | Weisman |
| 4,643,727 A | 2/1987 | Rosenbaum |
| 4,662,875 A | 5/1987 | Hirotsu |
| 4,662,877 A | 5/1987 | Williams |
| 4,670,011 A | 6/1987 | Mesek |
| 4,678,464 A | 7/1987 | Holtman |
| 4,695,278 A | 9/1987 | Lawson |
| 4,704,115 A | 11/1987 | Buell |
| 4,715,918 A | 12/1987 | Lang |
| 4,723,953 A | 2/1988 | Pratt et al. |
| 4,731,065 A | 3/1988 | Yamada |
| RE32,649 E | 4/1988 | Brandt et al. |
| 4,795,454 A | 1/1989 | Dragoo |
| 4,808,178 A | 2/1989 | Aziz |
| 4,834,735 A | 5/1989 | Alemany |
| 4,847,134 A | 7/1989 | Logsdon et al. |
| 4,848,815 A | 7/1989 | Molloy |
| 4,869,724 A | 9/1989 | Scripps |
| 4,888,231 A | 12/1989 | Angstadt |
| 4,892,535 A | 1/1990 | Bjoernberg et al. |
| 4,909,803 A | 3/1990 | Aziz |
| 4,940,464 A | 7/1990 | Van Gompel |
| 4,950,264 A | 8/1990 | Osborn, III |
| 4,960,477 A | 10/1990 | Mesek |
| 4,988,344 A | 1/1991 | Reising et al. |
| 4,990,147 A | 2/1991 | Freeland |
| 4,994,053 A | 2/1991 | Lang |
| 5,019,070 A | 5/1991 | Ruben |
| 5,032,120 A | 7/1991 | Freeland et al. |
| 5,037,416 A | 8/1991 | Allen |
| 5,062,840 A | 11/1991 | Holt et al. |
| 5,087,255 A | 2/1992 | Sims |
| 5,092,861 A | 3/1992 | Nomura |
| 5,124,188 A | 6/1992 | Roe et al. |
| 5,137,537 A | 8/1992 | Herron |
| 5,143,679 A | 9/1992 | Weber |
| 5,149,335 A | 9/1992 | Kellenberger |
| 5,151,091 A | 9/1992 | Glaug et al. |
| 5,151,092 A | 9/1992 | Buell |
| 5,156,793 A | 10/1992 | Buell |
| 5,167,897 A | 12/1992 | Weber |
| 5,242,436 A | 9/1993 | Weil |
| 5,246,433 A | 9/1993 | Hasse |
| 5,260,345 A | 11/1993 | Desmarais |
| 5,269,775 A | 12/1993 | Freeland |
| 5,300,053 A | 4/1994 | Genaro |
| 5,306,266 A | 4/1994 | Freeland |
| 5,342,338 A | 8/1994 | Roe |
| 5,383,869 A | 1/1995 | Osborn, III |
| 5,387,207 A | 2/1995 | Dyer |
| 5,397,316 A | 3/1995 | Young |
| 5,401,792 A | 3/1995 | Babu et al. |
| 5,411,497 A | 5/1995 | Tanzer |
| 5,425,725 A | 6/1995 | Tanzer |
| 5,460,622 A | 10/1995 | Dragoo et al. |
| 5,462,541 A | 10/1995 | Bruemmer et al. |
| 5,500,270 A | 3/1996 | Langdon et al. |
| 5,505,720 A | 4/1996 | Hujber et al. |
| 5,518,801 A | 5/1996 | Chappell |
| 5,527,300 A | 6/1996 | Sauer |
| 5,554,145 A | 9/1996 | Roe |
| 5,562,646 A | 10/1996 | Goldman |
| 5,569,234 A | 10/1996 | Buell |
| 5,571,096 A | 11/1996 | Dobrin |
| 5,591,155 A | 1/1997 | Nishikawa |
| 5,593,399 A | 1/1997 | Tanzer |
| 5,599,335 A | 2/1997 | Goldman |
| 5,601,542 A | 2/1997 | Melius |
| 5,625,222 A | 4/1997 | Yoneda |
| 5,628,741 A | 5/1997 | Buell et al. |
| 5,643,238 A | 7/1997 | Baker |
| 5,658,268 A | 8/1997 | Johns et al. |
| 5,662,634 A | 9/1997 | Yamamoto et al. |
| 5,762,641 A | 6/1998 | Bewick-sonntag |
| 5,788,684 A | 8/1998 | Abuto et al. |
| 5,803,920 A | 9/1998 | Gilman |
| 5,833,678 A | 11/1998 | Ashton et al. |
| 5,846,231 A | 12/1998 | Fujioka et al. |
| 5,855,572 A | 1/1999 | Schmidt |
| 5,868,724 A | 2/1999 | Dierckes, Jr. et al. |
| 5,895,379 A | 4/1999 | Litchholt et al. |
| 5,897,545 A | 4/1999 | Kline |
| 5,938,650 A | 8/1999 | Baer et al. |
| 5,941,863 A | 8/1999 | Guidotti et al. |
| 5,944,706 A | 8/1999 | Palumbo et al. |
| 5,957,908 A | 9/1999 | Kline |
| 6,004,306 A | 12/1999 | Robles |
| 6,048,489 A | 4/2000 | Reiter et al. |
| 6,054,631 A | 4/2000 | Gent |
| 6,090,994 A | 7/2000 | Chen |
| 6,099,515 A | 8/2000 | Sugito |
| 6,103,358 A | 8/2000 | Brueggemann et al. |
| 6,120,487 A | 9/2000 | Ashton |
| 6,120,489 A | 9/2000 | Johnson |
| 6,132,409 A | 10/2000 | Vogt et al. |
| 6,132,411 A | 10/2000 | Huber et al. |
| 6,133,501 A | 10/2000 | Hallock et al. |
| 6,231,556 B1 | 5/2001 | Osborn, III |
| 6,241,714 B1 | 6/2001 | Raidel et al. |
| 6,258,996 B1 | 7/2001 | Goldman |
| 6,293,933 B1 | 9/2001 | Ahlstrand |
| 6,368,687 B1 | 4/2002 | Joseph et al. |
| 6,372,952 B1 | 4/2002 | Lash et al. |
| 6,376,034 B1 | 4/2002 | Brander |
| 6,383,431 B1 | 5/2002 | Dobrin |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,458,111 B1 | 10/2002 | Onishi et al. |
| 6,458,877 B1 | 10/2002 | Ahmed et al. |
| 6,503,598 B1 | 1/2003 | Goda |
| 6,570,056 B1 | 5/2003 | Tanzer et al. |
| 6,602,234 B2 | 8/2003 | Klemp et al. |
| 6,645,569 B2 | 11/2003 | Cramer |
| 6,863,933 B2 | 3/2005 | Cramer |
| 6,972,011 B2 | 12/2005 | Mori |
| 7,108,916 B2 | 9/2006 | Ehrnsperger |
| 7,112,621 B2 | 9/2006 | Rohrbaugh |
| 7,122,023 B1 | 10/2006 | Hinoki |

(56) References Cited

U.S. PATENT DOCUMENTS

| | | | |
|---|---|---|---|
| 7,153,295 | B2 | 12/2006 | Nakajima et al. |
| 7,252,657 | B2 | 8/2007 | Mishima et al. |
| 7,666,174 | B2 | 2/2010 | Onishi et al. |
| 7,717,893 | B2 | 5/2010 | Hird et al. |
| 7,736,349 | B2 | 6/2010 | Gagliardi et al. |
| 7,744,576 | B2 | 6/2010 | Busam |
| 7,851,667 | B2 | 12/2010 | Becker et al. |
| 8,258,367 | B2 | 9/2012 | Lawson et al. |
| 8,343,296 | B2 | 1/2013 | Blessing et al. |
| 9,044,359 | B2 | 6/2015 | Wciorka et al. |
| 10,434,018 | B2 | 10/2019 | Wciorka et al. |
| 11,083,644 | B2 | 8/2021 | Wciorka et al. |
| 11,083,645 | B2 | 8/2021 | Wciorka et al. |
| 2001/0014797 | A1 | 8/2001 | Suzuki |
| 2001/0031954 | A1* | 10/2001 | Jordan .............. A61F 13/51496 604/385.01 |
| 2002/0007169 | A1 | 1/2002 | Graef |
| 2002/0013567 | A1 | 1/2002 | Mishima et al. |
| 2002/0049417 | A1 | 4/2002 | Onishi et al. |
| 2002/0102392 | A1 | 8/2002 | Fish et al. |
| 2002/0115969 | A1 | 8/2002 | Mori et al. |
| 2002/0151634 | A1 | 10/2002 | Rohrbaugh et al. |
| 2002/0192366 | A1 | 12/2002 | Cramer et al. |
| 2003/0018313 | A1 | 1/2003 | Tanzer et al. |
| 2003/0073967 | A1 | 4/2003 | Wahlström et al. |
| 2003/0105190 | A1 | 6/2003 | Diehl |
| 2003/0114816 | A1 | 6/2003 | Underhill et al. |
| 2003/0148684 | A1 | 8/2003 | Cramer et al. |
| 2003/0233082 | A1 | 12/2003 | Kline |
| 2004/0054344 | A1 | 3/2004 | Roettger et al. |
| 2004/0092900 | A1 | 5/2004 | Hoffman et al. |
| 2004/0097895 | A1 | 5/2004 | Busam |
| 2004/0111074 | A1 | 6/2004 | Eliasson |
| 2004/0158212 | A1 | 8/2004 | Ponomarenko |
| 2004/0162536 | A1 | 8/2004 | Becker |
| 2004/0167486 | A1 | 8/2004 | Busam |
| 2004/0193129 | A1 | 9/2004 | Guidotti et al. |
| 2004/0243078 | A1 | 12/2004 | Guidotti et al. |
| 2004/0243081 | A1 | 12/2004 | Suzuki |
| 2005/0003191 | A1 | 1/2005 | Ehrnsperger et al. |
| 2005/0008839 | A1 | 1/2005 | Cramer |
| 2005/0054999 | A1 | 3/2005 | Morman et al. |
| 2005/0055000 | A1 | 3/2005 | Ohnishi |
| 2005/0124953 | A1 | 6/2005 | Woltman et al. |
| 2005/0148983 | A1 | 7/2005 | Doverbo |
| 2005/0148989 | A1 | 7/2005 | Otsubo |
| 2005/0159720 | A1 | 7/2005 | Gentilcore |
| 2005/0182382 | A1 | 8/2005 | Bailey |
| 2005/0288645 | A1 | 12/2005 | Lavon |
| 2006/0058750 | A1 | 3/2006 | Di Girolamo et al. |
| 2006/0155254 | A1 | 7/2006 | Sanz et al. |
| 2006/0167424 | A1 | 7/2006 | Chang et al. |
| 2006/0177647 | A1 | 8/2006 | Schmidt |
| 2006/0184146 | A1 | 8/2006 | Suzuki |
| 2006/0184151 | A1* | 8/2006 | Onishi .............. A61F 13/15203 604/385.24 |
| 2006/0240229 | A1 | 10/2006 | Ehrnsperger et al. |
| 2007/0027435 | A1 | 2/2007 | Nakagawa et al. |
| 2007/0027436 | A1 | 2/2007 | Nakagawa et al. |
| 2007/0043330 | A1 | 2/2007 | Lankhof |
| 2007/0088308 | A1 | 4/2007 | Ehrnsperger et al. |
| 2007/0093164 | A1 | 4/2007 | Nakaoka |
| 2007/0106240 | A1 | 5/2007 | Nakajima et al. |
| 2007/0118087 | A1 | 5/2007 | Flohr |
| 2007/0142802 | A1 | 6/2007 | Suzuki |
| 2007/0156108 | A1 | 7/2007 | Becker et al. |
| 2007/0167928 | A1 | 7/2007 | Becker et al. |
| 2007/0179464 | A1 | 8/2007 | Becker et al. |
| 2007/0179469 | A1 | 8/2007 | Takahashi et al. |
| 2007/0197992 | A1 | 8/2007 | Martynus et al. |
| 2007/0219521 | A1 | 9/2007 | Hird |
| 2007/0250026 | A1 | 10/2007 | Venturino et al. |
| 2007/0287983 | A1 | 12/2007 | Lodge |
| 2008/0058752 | A1 | 3/2008 | Wciorka et al. |
| 2008/0132864 | A1 | 6/2008 | Lawson et al. |
| 2008/0147024 | A1 | 6/2008 | Potts et al. |
| 2008/0312617 | A1 | 12/2008 | Hundorf |
| 2008/0312625 | A1 | 12/2008 | Hundorf et al. |
| 2008/0312628 | A1 | 12/2008 | Hundorf et al. |
| 2010/0256586 | A1 | 10/2010 | Bergstroem et al. |
| 2010/0268185 | A1 | 10/2010 | Halleroed et al. |
| 2010/0331801 | A1 | 12/2010 | Kawakami et al. |
| 2011/0041999 | A1 | 2/2011 | Hundorf et al. |
| 2012/0316528 | A1 | 12/2012 | Kreuzer et al. |
| 2015/0057631 | A1 | 2/2015 | Dieringer et al. |
| 2016/0158075 | A1 | 6/2016 | Sheldon et al. |
| 2018/0228674 | A1 | 8/2018 | Wciorka et al. |
| 2019/0336361 | A1 | 11/2019 | Wciorka et al. |
| 2021/0259896 | A1 | 8/2021 | Wciorka et al. |
| 2022/0015965 | A1 | 1/2022 | Wciorka et al. |
| 2022/0023117 | A1 | 1/2022 | Wciorka et al. |

FOREIGN PATENT DOCUMENTS

| | | |
|---|---|---|
| EP | 0518340 A1 | 12/1992 |
| EP | 0640330 A1 | 3/1995 |
| EP | 1057464 A2 | 12/2000 |
| EP | 1088537 A2 | 4/2001 |
| EP | 1201212 A2 | 5/2002 |
| EP | 1447006 A1 | 8/2004 |
| EP | 1493413 A2 | 1/2005 |
| EP | 1621167 A2 | 2/2006 |
| JP | H06269475 A | 9/1994 |
| JP | 2002113800 A | 4/2002 |
| JP | 2002325799 A | 11/2002 |
| JP | 2006149457 A | 6/2006 |
| WO | 9511651 A1 | 5/1995 |
| WO | 9516746 A1 | 6/1995 |
| WO | 9711659 A1 | 4/1997 |
| WO | 9817219 A1 | 4/1998 |
| WO | 0115647 A1 | 3/2001 |
| WO | 0189439 A1 | 11/2001 |
| WO | 02064877 A2 | 8/2002 |
| WO | 2004071539 A3 | 12/2004 |
| WO | 2006062258 A2 | 6/2006 |
| WO | 2006074073 A1 | 7/2006 |
| WO | 2007014233 A1 | 2/2007 |
| WO | 2007014235 A1 | 2/2007 |

OTHER PUBLICATIONS

All Office Actions; U.S. Appl. No. 12/416,383, filed Apr. 1, 2009.
All Office Actions; U.S. Appl. No. 14/700,188, filed Apr. 30, 2015.
All Office Actions; U.S. Appl. No. 15/952,702, filed Apr. 13, 2018.
All Office Actions; U.S. Appl. No. 15/952,781, filed Apr. 13, 2018.
All Office Actions; U.S. Appl. No. 15/952,871, filed Apr. 13, 2018.
All Office Actions; U.S. Appl. No. 16/516,291, filed Jul. 19, 2019.
All Office Actions; U.S. Appl. No. 17/318,039, filed May 12, 2021.
All Office Actions; U.S. Appl. No. 17/489,832, filed Sep. 30, 2021.
All Office Actions; U.S. Appl. No. 17/492,725, filed Oct. 4, 2021.
Third Party Opposition filed for European Patent Application Ser. No.09739428.2, Dated Sep. 3, 2014; 20 pages.

* cited by examiner

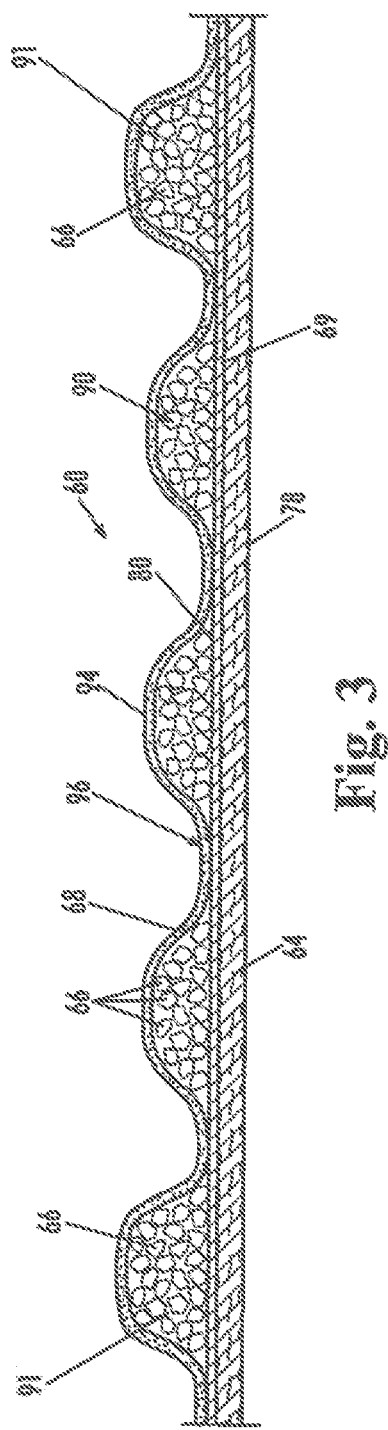

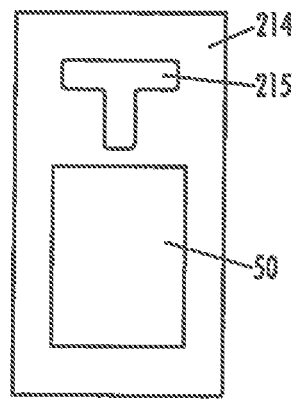 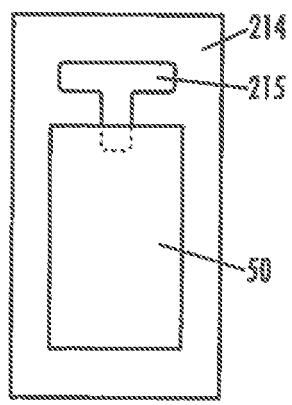 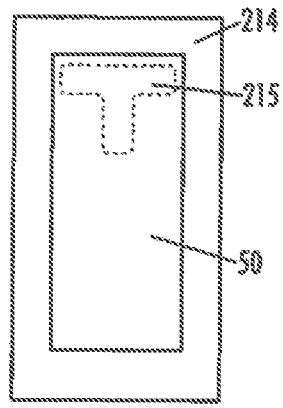
Fig. 27A    Fig. 27B    Fig. 27C
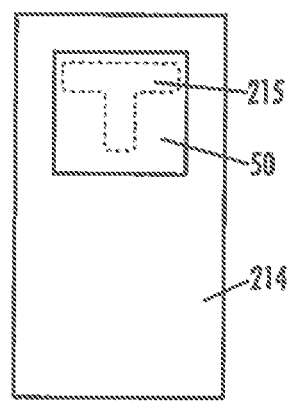 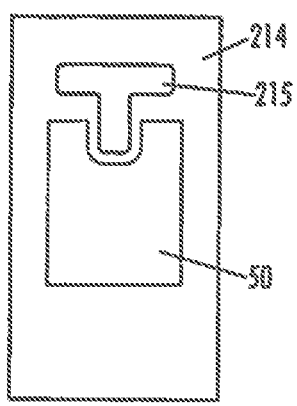
Fig. 27D    Fig. 27E

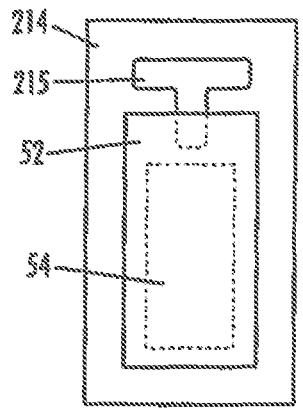
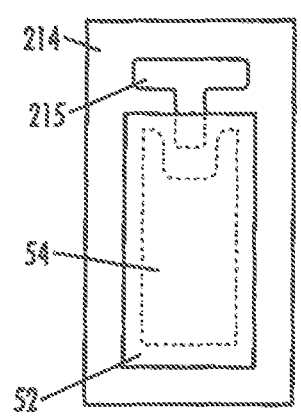
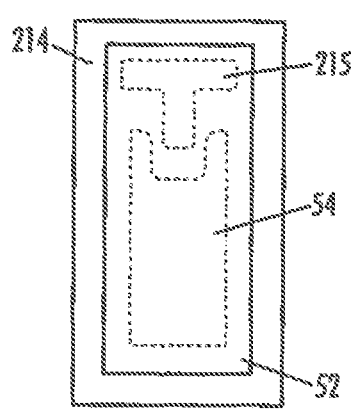
Fig. 27F     Fig. 27G     Fig. 27H
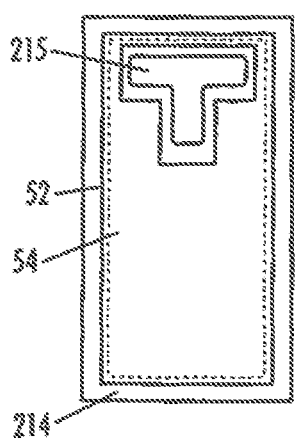
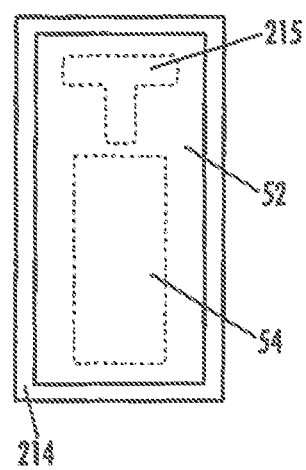
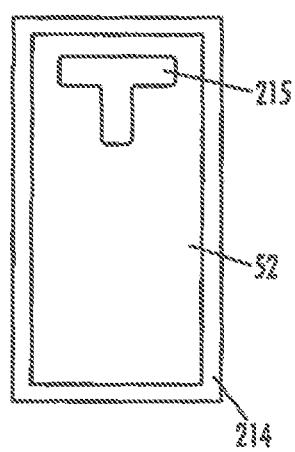
Fig. 27I     Fig. 27J     Fig. 27K

DISPOSABLE ABSORBENT ARTICLE

CROSS REFERENCE TO RELATED APPLICATIONS

This application is a continuation of U.S. patent application Ser. No. 17/318,039, filed on May 12, 2021, which is a continuation of U.S. patent application Ser. No. 15/952,702, filed on Apr. 13, 2018, now U.S. Pat. No. 11,083,644, issued on Aug. 10, 2021, which is a continuation of U.S. patent application Ser. No. 14/700,188, filed on Apr. 30, 2015, now U.S. Pat. No. 10,434,018, issued on Oct. 8, 2019, which is a continuation of U.S. patent application Ser. No. 12/416,383, filed on Apr. 1, 2009, now U.S. Pat. No. 9,044,359, issued on Jun. 2, 2015, which claims the benefit of U.S. Provisional Patent Application No. 61/048,668, filed on Apr. 29, 2008, the entire disclosures of all of which are fully incorporated herein by reference.

FIELD OF THE INVENTION

The present invention generally relates to an absorbent article, and more particularly to a disposable absorbent garment, such as a taped diaper or training pant, comprising absorbent particulate polymer material.

BACKGROUND OF THE INVENTION

Absorbent articles, such as disposable diapers, training pants, and adult incontinence undergarments, absorb and contain body exudates.

Fecal material is often difficult to remove from the skin of the user (e.g., wearer) of the absorbent article, in particular on sensitive skin such as that of young babies. Moreover, it is known that fecal material on the skin can cause irritation and redness of the skin and sometimes even dermatitis. Hence it desirable to reduce the fecal material on the skin, to provide a means to isolate the fecal material immediately after discharge, away from the skin. Conventional approaches toward this isolation include providing a diaper with a top sheet with one or more openings, through which the feces can pass for storage underneath this top sheet, away from the skin. However, this approach may not always be effective, particularly when the baby is in a sitting position or when the diaper is already highly urine-loaded, both of which diminish the void volume available to receive the feces.

There is also a desire to improve the comfort and fit of absorbent articles such as diapers, for example to make them thinner and more flexible while preserving or enhancing the article's ability to absorb and hold one or more gushes of liquid, to minimize uncontrolled bowel movement spreading, and to capture bowel movements so as to lead to cleaner skin for the wearer, with consequently less skin irritation and easier clean up.

SUMMARY OF THE INVENTION

The present invention addresses one or more technical problems described above and provides a disposable absorbent article, which may comprise a chassis and an absorbent core, which may be substantially cellulose free. The chassis may include a top sheet and a back sheet. The absorbent core may be located between the top sheet and the back sheet and may comprise an absorbent particulate polymer material. The absorbent core includes at least one cavity, which may be defined at least about its perimeter by the absorbent particulate polymer material. The at least one cavity may be substantially free of the absorbent particulate polymer material. In one embodiment, the void volume of the cavity may be from about 2 ml to about 70 ml.

In one embodiment, the absorbent particulate polymer material present in the absorbent core may have a basis weight that varies across the absorbent core in a direction substantially perpendicular to the central longitudinal axis, in a direction substantially parallel to the central longitudinal axis, or in both directions.

In one embodiment, the disposable absorbent article may have a central longitudinal axis extending from a first end to a second end, and the at least one cavity may include (i) a first channel elongated in a direction substantially parallel to and located about the central longitudinal axis, and (ii) a second channel elongated in a direction substantially perpendicular to the central longitudinal axis. The first and second channels of the cavity together may form a T-shape.

In certain embodiments, the first channel may have a width from about 5% to about 60% of the width of the absorbent core and a length from about 2% to about 50% of the length of the absorbent core. The second channel may have a width from about 25% to about 90% of the width of the absorbent core and a length from about 2% to about 40% of the length of the absorbent core. In one embodiment, the first channel of the cavity may have a width between about 10 mm and about 40 mm, and a length between about 10 mm and about 130 mm. In another embodiment, the second channel of the cavity may have a width between about 30 mm and about 110 mm, and a length between about 10 mm and about 100 mm. Combinations of the first and second channels with these dimension ratios and values are contemplated.

In one embodiment, the absorbent core may comprise a core cover and a dusting layer adhered to one another about the periphery of the absorbent core to form an envelope about the absorbent particulate polymer materials to hold the absorbent particulate polymer material within the absorbent core. The core cover and the dusting layer may be adhered to one another about an area defining the bottom of the at least one cavity.

In one embodiment, the disposable absorbent article may further include an acquisition system located between the absorbent core and the top sheet. In one embodiment, the acquisition system may include an upper acquisition layer, which faces the top sheet, and a lower acquisition layer, which faces the absorbent core. In one case, the lower acquisition layer does not cover the at least one cavity. In one case, the upper acquisition layer does not completely cover the at least one cavity. The at least one cavity may further be defined about its perimeter by interior edges of an aperture in the acquisition system.

In a certain embodiment, the top sheet of the disposable absorbent article is an elasticized top sheet having at least one opening. At least a portion of the opening may be substantially aligned with the first channel of the cavity in the absorbent core.

In certain embodiments, the disposable absorbent article may be a diaper or a pant. In one example, the first channel of the cavity is located in the absorbent core along the central longitudinal axis of the diaper or pant at a position which, when the diaper or pant is worn by a wearer, will be in alignment with a predetermined region about the anus of the wearer.

In another aspect, a method is provided for making an absorbent core for use in a disposable absorbent article. The method may comprise depositing an absorbent particulate polymer material on a first substrate to form an absorbent core having a central longitudinal axis extending from a first end to a second end, such that the absorbent core is substantially cellulose free and comprises at least one cavity defined at least about its perimeter by the absorbent particulate polymer material. The at least one cavity may be substantially free of absorbent particulate polymer material.

In one embodiment, the step of depositing may comprise placing the first substrate on a porous forming surface and depositing the absorbent particulate polymer material to the substrate while applying a vacuum to the substrate through the porous forming surface. In one example, the forming surface may have recesses for receiving the substrate and the absorbent particulate polymer material and the recesses may be sized and arranged to vary the basis weight of the absorbent particulate polymer material across the substrate. In another example, the vacuum applied to the substrate may vary across the forming surface so as to vary the basis weight of the absorbent particulate polymer material across the substrate.

In another embodiment, the step of depositing may further comprise pneumatically delivering the absorbent particulate polymer material to the substrate and varying the pneumatic delivery to the forming surface so as to vary the amount of absorbent particulate polymer material across the substrate. In one embodiment, the method may further include adhering the first substrate to a second substrate about their peripheries to form an envelope about the absorbent particulate polymer material to hold the absorbent particulate polymer material within the absorbent core.

In one embodiment, the first substrate and the second substrate may be adhered to one another about an area defining the bottom of the at least one cavity. In one embodiment, the at least one cavity may be stamped into the absorbent core.

In still another aspect, a method is provided for making a disposable absorbent article. The method may comprise depositing an absorbent particulate polymer material on a substrate to form an absorbent core which is substantially cellulose free; forming at least one cavity in the absorbent core, said at least one cavity being defined at least about its perimeter by the absorbent particulate polymer material; and locating the absorbent core between a top sheet and a back sheet of a chassis. In one embodiment, the method may further include adhering a core cover and a dusting layer to one another about a periphery of the absorbent core to form an envelope about the absorbent particulate polymer materials to hold the absorbent particulate polymer material within the absorbent core. In one case, the method may further include adhering the core cover and the dusting layer to one another at an area about the bottom of the at least one cavity. In one embodiment, the method may further include locating an acquisition system between the top sheet and the absorbent core.

Features and advantages of the invention may be apparent from the following detailed description, drawings, and claims.

BRIEF DESCRIPTION OF THE DRAWINGS

FIG. 3 is a partial cross sectional view of an absorbent core layer in accordance with an embodiment of this invention wherein more absorbent particulate polymer material is present toward lateral edges of the diaper than in a central zone of the diaper.
FIG. 4 is a partial cross sectional view of an absorbent core layer in accordance with another embodiment of this invention.

FIGS. 27A-K are plan views of several absorbent cores having cavities and different acquisition system designs, according to certain embodiments of the invention.

DETAILED DESCRIPTION OF THE INVENTION

Figure 1:
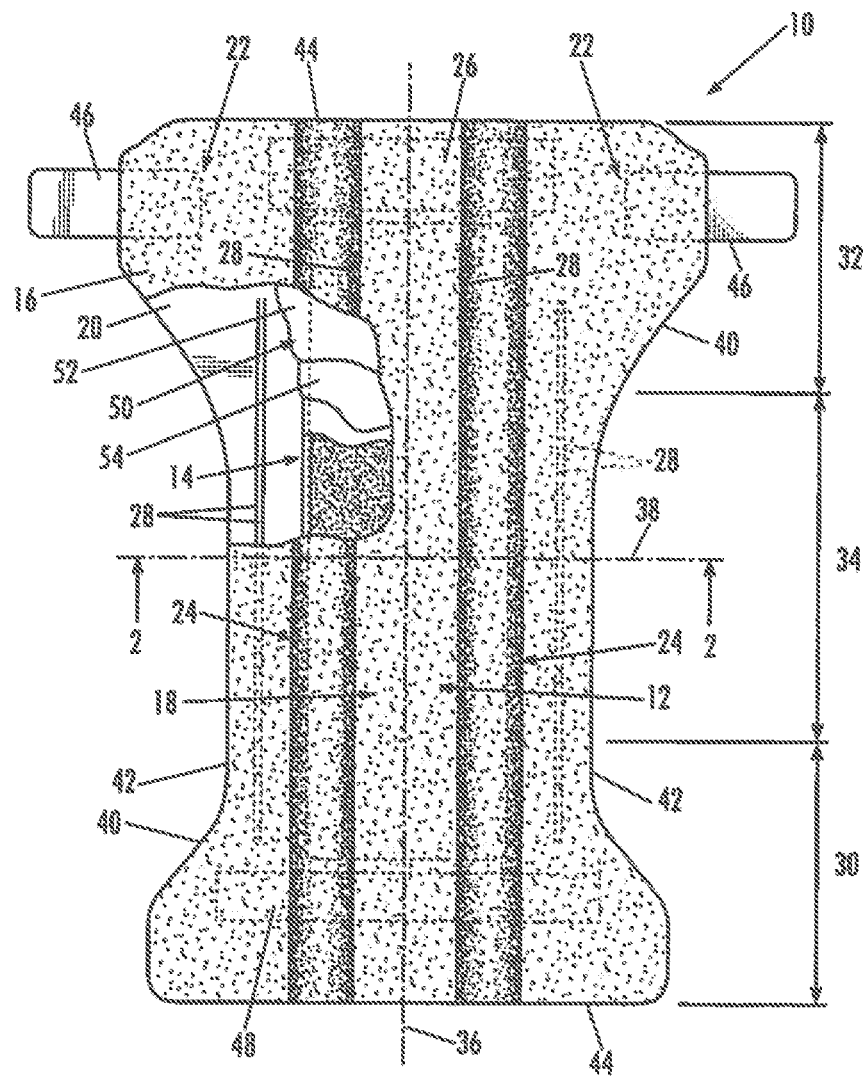
FIG. 1 is a plan view of a diaper in accordance with an embodiment of the present invention.

A disposable absorbent article has been developed which comprises a chassis, which may include a top sheet and a back sheet, and an absorbent core which may be located between the top sheet and the back sheet and may comprise an absorbent particulate polymer material. The absorbent core may include one or more cavities, for accommodating a bowel movement, defined at least about its perimeter by the absorbent particulate polymer material redistributed (versus cavity-less core) whilst maintaining overall liquid containment capacity. In a certain embodiment, the disposable absorbent article may have a central longitudinal axis extending from a first end to a second end, and the cavity may include (i) a first channel elongated in a direction substantially parallel to and located about the central longitudinal axis, and (ii) a second channel elongated in a direction substantially perpendicular to the central longitudinal axis. The disposable absorbent article optionally may further include an elasticized top sheet located adjacent the top sheet and having at least one opening, a portion of which may be substantially aligned with the first channel of the cavity in the absorbent core. Embodiments of such disposable absorbent articles are described hereinbelow along with embodiments of apparatuses and methods for making such disposable absorbent articles.

Definitions

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" means a structure typically disposed between a top sheet and cover sheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core may be substantially cellulose free. The absorbent core does not include an acquisition system, a top sheet, or a back sheet of the absorbent article. In a certain embodiment, the absorbent core would consist essentially of the one or more substrates, the absorbent polymer material, the thermoplastic composition, and optionally the cover layer. In another embodiment, the amount of absorbent particulate polymer material present in the absorbent core may vary across the absorbent core.

"Absorbent polymer material," "absorbent gelling material," "AGM," "super absorbent," and "super absorbent material" are used herein interchangeably and refer to cross linked polymeric materials that can absorb at least 5 times their weight of an aqueous fluid such as 0.9% saline as measured using the Centrifuge Retention Capacity test.

"Absorbent particulate polymer material" is used herein to refer to an absorbent polymer material which is in particulate form so as to be flowable in the dry state.

"Airfelt" is used herein to refer to comminuted wood pulp, which is a form of cellulosic fiber.

"Basis weight" means weight of a material per unit area of the material.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Disposable" is used in its ordinary sense to mean an article that is disposed or discarded after a limited number of usage events over varying lengths of time, such as less than about 20 events, or less than about 10 events, or less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Fiber" and "filament" are used interchangeably.

"Hydrophilic" describes fibers or surfaces of fibers, which are wettable by aqueous fluids (e.g. aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

"Substantially cellulose free" is used herein to describe an article, such as an absorbent core, that contains less than about 10% by weight cellulosic fibers, less than about 5% cellulosic fibers, less than about 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substantially continuously distributed", as used herein, refers to absorbent particulate polymer material that is arranged across the absorbent particulate polymer material area. Optionally, the absorbent particulate polymer material may be arranged such that the substrate layers do not touch in zones 122 and 124. In one embodiment, the substrate layers may touch in the peripheral areas outside the absorbent particulate polymer material area. It is important to note that the thermoplastic material used in the presently described disposable absorbent articles does not interrupt the substantially continuously distributed absorbent particulate polymer material. Thus, the substantially continuously distributed absorbent particulate polymer material includes the thermoplastic material.

"Substantially free of absorbent particulate polymer material", as used herein, refers to the one or more cavities of the absorbent core having an area (in plan view) in which the absorbent particulate polymer material is present in an amount not exceeding 10% of the basis weight of absorbent particulate polymer material in the area of the absorbent core surrounding the one or more cavities.

"Thickness" and "caliper" are used herein interchangeably.

Absorbent Articles

FIG. 1 is a plan view of a diaper 10 according to a certain embodiment of the present invention. The diaper 10 is shown in its flat out, uncontracted state (i.e., without elastic induced contraction) and portions of the diaper 10 are cut away to more clearly show the underlying structure of the diaper 10. A portion of the diaper 10 that contacts a wearer is facing the viewer in FIG. 1. The diaper 10 generally may comprise a chassis 12 and an absorbent core 14 disposed in the chassis.

The chassis 12 of the diaper 10 in FIG. 1 may comprise the main body of the diaper 10. The chassis 12 may comprise an outer covering 16 including a top sheet 18, which may be liquid pervious, and/or a back sheet 20, which may be liquid impervious. The absorbent core 14 may be encased between the top sheet 18 and the back sheet 20. The chassis 12 may also include side panels 22, elasticized leg cuffs 24, and an elastic waist feature 26.

The leg cuffs 24 and the elastic waist feature 26 may each typically comprise elastic members 28. One end portion of the diaper 10 may be configured as a first waist region 30 of the diaper 10. An opposite end portion of the diaper 10 may be configured as a second waist region 32 of the diaper 10. An intermediate portion of the diaper 10 may be configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 is depicted in FIG. 1 with its central longitudinal axis 36 and its transverse axis 38. The periphery 40 of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper 10. The chassis 12 may also comprise a fastening system, which may include at least one fastening member 46 and at least one stored landing zone 48.

The diaper 10 may also include such other features as are known in the art including front and rear ear panels, waist cap features, elastics and the like to provide better fit, containment and aesthetic characteristics. Such additional features are well known in the art and are e.g., described in U.S. Pat. Nos. 3,860,003 and 5,151,092.

In order to keep the diaper 10 in place about the wearer, at least a portion of the first waist region 30 may be attached by the fastening member 46 to at least a portion of the second waist region 32 to form leg opening(s) and an article waist. When fastened, the fastening system carries a tensile load around the article waist. The fastening system may allow an article user to hold one element of the fastening system, such as the fastening member 46, and connect the first waist region 30 to the second waist region 32 in at least two places. This may be achieved through manipulation of bond strengths between the fastening device elements.

According to certain embodiments, the diaper 10 may be provided with a re-closable fastening system or may alternatively provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to the chassis and to each other to form a pant. The fastening system and any component thereof may include any material suitable for such a use, including but not limited to plastics, films, foams, nonwoven webs, woven webs, paper, laminates, fiber reinforced plastics and the like, or combinations thereof. In certain embodiments, the materials making up the fastening device may be flexible. The flexibility may allow the fastening system to conform to the shape of the body and thus, reduce the likelihood that the fastening system will irritate or injure the wearer's skin.

For unitary absorbent articles, the chassis 12 and absorbent core 14 may form the main structure of the diaper 10 with other features added to form the composite diaper structure. While the top sheet 18, the back sheet 20, and the absorbent core 14 may be assembled in a variety of well-known configurations, certain diaper configurations are described generally in U.S. Pat. No. 5,554,145 to Roe et al.; U.S. Pat. No. 5,569,234 to Buell et al.; and U.S. Pat. No. 6,004,306 to Robles et al. on Dec. 21, 1999.

The top sheet 18 in FIG. 1 may be fully or partially elasticized or may be foreshortened to provide a void space between the top sheet 18 and the absorbent core 14. Exemplary structures including elasticized or foreshortened top sheets are described in more detail in U.S. Pat. No. 5,037,416 to Allen et al.; and U.S. Pat. No. 5,269,775 to Freeland et al.

The back sheet 20 may be joined with the top sheet 18. The back sheet 20 may prevent the exudates absorbed by the absorbent core 14 and contained within the diaper 10 from soiling other external articles that may contact the diaper 10, such as bed sheets and undergarments. In certain embodiments, the back sheet 20 may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable back sheet films include those manufactured by Tredegar Industries Inc. (Terre Haute, Indiana) and sold under the trade names X15306, X10962, and X10964. Other suitable back sheet materials may include breathable materials that permit vapors to escape from the diaper 10 while still preventing exudates from passing through the back sheet 10. Exemplary breathable materials may include materials such as woven webs, nonwoven webs, composite materials such as film-coated nonwoven webs, and microporous films such as manufactured by Mitsui Toatsu Co. (Japan) under the designation ESPOIR NO and by EXXON Chemical Co. (Bay City, Texas) under the designation EXXAIRE. Suitable breathable composite materials comprising polymer blends are available from Clopay Corporation (Cincinnati, Ohio) under the name HYTREL blend P18-3097. Such breathable composite materials are described in PCT Application No. WO 95/16746, published Jun. 22, 1995 in the name of E.I. DuPont. Other breathable back sheets including nonwoven webs and apertured formed films are described in U.S. Pat. No. 5,571,096 to Dobrin et al.

Figure 2:
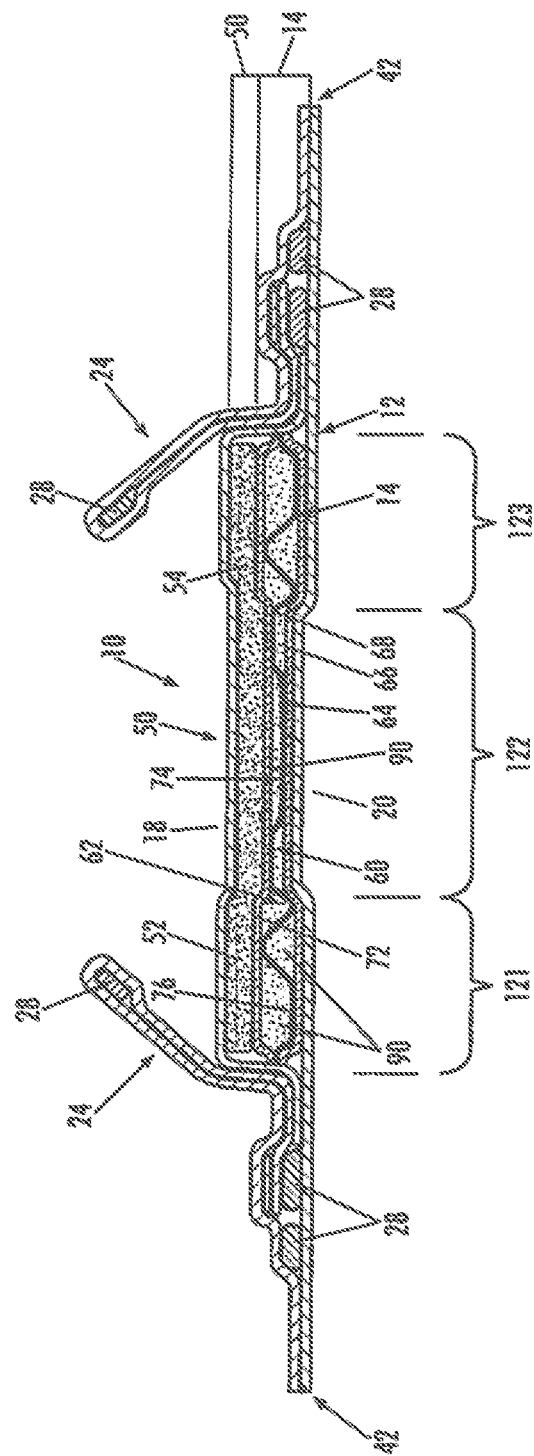
FIG. 2 is a cross sectional view of the diaper shown in FIG. 1 taken along the sectional line 2-2 of FIG. 1.

FIG. 2 shows a cross section of FIG. 1 taken along the sectional line 2-2 of FIG. 1. Starting from the wearer facing side, the diaper 10 may comprise the top sheet 18, the components of the absorbent core 14, and the back sheet 20. According to a certain embodiment, diaper 10 may also comprise an acquisition system 50 disposed between the liquid permeable top sheet 18 and a wearer facing side of the absorbent core 14. The acquisition system 50 may be in direct contact with the absorbent core. The acquisition system 50 may comprise a single layer or multiple layers, such as an upper acquisition layer 52 facing the towards the wearer's skin and a lower acquisition 54 layer facing the garment of the wearer. According to a certain embodiment, the acquisition system 50 may function to receive a surge of liquid, such as a gush of urine, and quickly absorb the liquid and distribute it across the absorbent core 14 so that the absorbent core absorbs the liquid before the liquid flows beyond the absorbent layer 14 and out of the diaper 10. In other words, the acquisition system 50 may serve as a temporary reservoir for liquid until the absorbent core 14 can absorb the liquid.

In a certain embodiment, the acquisition system 50 may comprise chemically cross-linked cellulosic fibers. Such cross-linked cellulosic fibers may have desirable absorbency properties. Exemplary chemically cross-linked cellulosic fibers are disclosed in U.S. Pat. No. 5,137,537 which is incorporated herein by reference. In certain embodiments, the chemically cross-linked cellulosic fibers have between about 0.5 mole % and about 10.0 mole % of a $C_2$ to $C_9$ polycarboxylic cross-linking agent or between about 1.5 mole % and about 6.0 mole % of a $C_2$ to $C_9$ polycarboxylic cross-linking agent. Citric acid is an exemplary cross-linking agent. In other embodiments, polyacrylic acids may be used. Further, according to certain embodiments, the cross-linked cellulosic fibers have a water retention value of about 25 to about 60, or about 28 to about 50, or about 30 to about 45. A method for determining water retention value is disclosed in U.S. Pat. No. 5,137,537. According to certain embodiments, the cross-linked cellulosic fibers may be crimped, twisted, or curled, or a combination thereof including crimped, twisted, and curled.

In a certain embodiment, one or both of the upper and lower acquisition layers 52 and 54 may comprise a nonwoven, which may be hydrophilic. Further, according to a certain embodiment, one or both of the upper and lower acquisition layers 52 and 54 may comprise the chemically cross-linked cellulosic fibers, which may or may not form part of a nonwoven material. According to an exemplary embodiment, the upper acquisition layer 52 may comprise a nonwoven, without the cross-linked cellulosic fibers, and the lower acquisition layer 54 may comprise the chemically cross-linked cellulosic fibers. Further, according to an embodiment, the lower acquisition layer 54 may comprise the chemically cross-linked cellulosic fibers mixed with other fibers such as natural or synthetic polymeric fibers. According to exemplary embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof. According to a one embodiment, the lower acquisition layer 54 has a total dry weight, the cross-linked cellulosic fibers are present on a dry weight basis in the first acquisition layer in an amount from about 30% to about 95% by weight of the lower acquisition layer 54, and the other natural or synthetic polymeric fibers are present on a dry weight basis in the lower acquisition layer 54 in an amount from about 70% to about 5% by weight of the lower acquisition layer 54. According to another embodiment, the cross-linked cellulosic fibers are present on a dry weight basis in the first acquisition layer in an amount from about 80% to about 90% by weight of the lower acquisition layer 54, and the other natural or synthetic polymeric fibers are present on a dry weight basis in the lower acquisition layer 54 in an amount from about 20% to about 10% by weight of the lower acquisition layer 54.

According to a certain embodiment, the lower acquisition layer 54 desirably has a high fluid uptake capability. Fluid uptake is measured in grams of absorbed fluid per gram of absorbent material and is expressed by the value of "maximum uptake." A high fluid uptake corresponds therefore to a high capacity of the material and is beneficial, because it ensures the complete acquisition of fluids to be absorbed by an acquisition material. According to exemplary embodiments, the lower acquisition layer 54 has a maximum uptake of about 10 g/g.

A relevant attribute of the lower acquisition layer 54 is its Medium Desorption Pressure (MDP) which is related to acquisition speed. The MDP is a measure of the capillary pressure that is required to dewater the lower acquisition layer 54 to about 50% of its capacity at 0 cm capillary suction height as derived from the Capillary Sorption test. Generally, a relatively lower MDP may be useful. The lower MDP may allow the lower acquisition layer 54 to more efficiently drain the acquisition material and utilize more of its capillary suction to distribute liquid to the absorbent core 14. Without wishing to be bound by theory, a given distribution material may have a definable capillary suction. The ability of the lower acquisition layer 54 to move liquid vertically via capillary forces will be directly impacted by the opposing capillary forces associated desorption. Minimizing these capillary forces may positively impact the performance of the lower acquisition layer 54. However, in a certain embodiment the lower acquisition layer 54 may also have adequate capillary absorption suction in order to drain the layers above (upper acquisition layer 52 and top sheet 18, in particular) and to temporarily hold liquid until the liquid can be partitioned away by the absorbent core components. Therefore, in a certain embodiment, the lower acquisition layer 54 may have a minimum MDP which should correspond to a height of greater than 5 cm. Further, according to exemplary embodiments, the lower acquisition layer 54 has an MDP value of less than about 20.5 cm $H_2O$, or less than about 19 cm $H_2O$, or less than about 18 cm $H_2O$ to provide for fast acquisition.

The methods for determining MDP and maximum uptake are disclosed in U.S. Patent Application Publication No. 2007/0118087 A1 (Flohr et al.), the disclosure of which is incorporated herein by reference.

For example, according to one embodiment, the lower acquisition layer 54 may comprise 7 about 0% by weight of chemically cross-linked cellulose fibers, about 10% by weight polyester (PET), and about 20% by weight untreated pulp fibers. According to a second embodiment, the lower acquisition layer 54 may comprise about 70% by weight chemically cross-linked cellulose fibers, about 20% by weight lyocell fibers, and about 10% by weight PET fibers. According to a third embodiment, the lower acquisition layer 54 may comprise about 68% by weight chemically cross-linked cellulose fibers, about 16% by weight untreated pulp fibers, and about 16% by weight PET fibers.

Suitable non-woven materials for the upper and lower acquisition layers 52 and 54 include, but are not limited to SMS material, comprising a spunbonded, a melt-blown and a further spunbonded layer. In certain embodiments, permanently hydrophilic non-wovens, and in particular, nonwovens with durably hydrophilic coatings are desirable. Another suitable embodiment comprises a SMMS-structure. In certain embodiments, the non-wovens are porous.

In certain embodiments, suitable non-woven materials may include, but are not limited to, synthetic fibers, such as PE, PET, and PP. As polymers used for nonwoven production may be inherently hydrophobic, they may be coated with hydrophilic coatings. One way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in U.S. Patent Application Publication No. 2004/0097895 A1 (Busam et al.). Another way to produce nonwovens with durably hydrophilic coatings is to coat the nonwoven with hydrophilic nanoparticles as described in U.S. Pat. No. 7,112,621 to Rohrbaugh et al. and PCT Application Publication WO 02/064877.

Typically, nanoparticles have a largest dimension of below 750 nm. Nanoparticles with sizes ranging form 2 to 750 nm may be economically produced. An advantage of nanoparticles is that many of them can be easily dispersed in water solution to enable coating application onto the nonwoven, they typically form transparent coatings, and the coatings applied from water solutions are typically sufficiently durable to exposure to water. Nanoparticles can be organic or inorganic, synthetic or natural. Inorganic nanoparticles generally exist as oxides, silicates, carbonates. Typical examples of suitable nanoparticles are layered clay minerals (e.g., LAPONITE™ from Southern Clay Products, Inc. (USA), and Boehmite alumina (e.g., Disperal P2™ from North American Sasol. Inc.). According to a certain embodiment, a suitable nanoparticle coated non-woven is that disclosed in U.S. Patent Application Publication No. 2004/0158212 (Ponomarenko et al.).

Further useful non-wovens are described in U.S. Pat. No. 6,645,569 to Cramer et al., U.S. Pat. No. 6,863,933 to Cramer et al., U.S. Pat. No. 7,112,621 to Rohrbaugh et al., U.S. Patent Application Publication No. 2003/0148684 (Cramer et al.), and U.S. Patent Application Publication No. 2005/0008839 (Cramer et al.)

In some cases, the nonwoven surface can be pre-treated with high energy treatment (corona, plasma) prior to application of nanoparticle coatings. High energy pre-treatment typically temporarily increases the surface energy of a low surface energy surface (such as PP) and thus enables better wetting of a nonwoven by the nanoparticle dispersion in water.

Notably, permanently hydrophilic non-wovens are also useful in other parts of an absorbent article. For example, top sheets and absorbent core layers comprising permanently hydrophilic non-wovens as described above have been found to work well.

According to a certain embodiment, the upper acquisition layer 52 may comprise a material that provides good recovery when external pressure is applied and removed. Further, according to a certain embodiment, the upper acquisition layer 52 may comprise a blend of different fibers selected, for example from the types of polymeric fibers described above. In some embodiments, at least a portion of the fibers may exhibit a spiral-crimp which has a helical shape. In some embodiments, the upper acquisition layer 52 may comprise fibers having different degrees or types of crimping, or both. For example, one embodiment may include a mixture of fibers having about 8 to about 12 crimps per inch (cpi) or about 9 to about 10 cpi, and other fibers having about 4 to about 8 cpi or about 5 to about 7 cpi. Different types of crimps include, but are not limited to, a 2D crimp or "flat crimp" and a 3D or spiral-crimp. According to a certain embodiment, the fibers may include bi-component fibers, which are individual fibers each comprising different materials, usually a first and a second polymeric material. It is believed that the use of side-by-side bi-component fibers is beneficial for imparting a spiral-crimp to the fibers.

The upper acquisition layer 52 may be stabilized by a latex binder, for example a styrene-butadiene latex binder (SB latex), in a certain embodiment. Processes for obtaining such lattices are known, for example, from EP 149 880 (Kwok) and U.S. Patent Application Publication No. 2003/0105190 (Diehl et al.). According to a certain embodiment, SB lattices may be obtained using more than about 10 weight % of a mono-, or bi-carboxylic acid, and will herein be referred to as having a carboxylation level of more than about 10%. Further, according to a certain embodiment, SB lattices may have a carboxylation level from about 10% to about 25%, for example about 10% to about 20%. In certain embodiments, the binder may be present in the upper acquisition layer 52 in excess of about 12%, about 14% or about 16% by weight. For certain embodiments, SB latex is available under the trade name GENFLO™ 3160 (OMNOVA Solutions Inc.; Akron, Ohio).

The absorbent core 14 in FIGS. 1-10 generally is disposed between the top sheet 18 and the back sheet 20 and comprises two layers, a first absorbent layer 60 and a second absorbent layer 62. As best shown in FIG. 3, the first absorbent layer 60 of the absorbent core 14 comprises a substrate 64, an absorbent particulate polymer material 66 on the substrate 64, and a thermoplastic composition 68 on the absorbent particulate polymer material 66 and at least portions of the first substrate 64 as an adhesive for covering and immobilizing the absorbent particulate polymer material 66 on the first substrate 64. According to another embodiment illustrated in FIG. 4, the first absorbent layer 60 of the absorbent core 14 may also include a cover layer 70 on the thermoplastic composition 68. The absorbent core 14 may also include another layer 69 of thermoplastic composition on the first substrate 64 for anchoring the absorbent particulate polymer material 66 to the first substrate 64.

Likewise, as best illustrated in FIG. 2, the second absorbent layer 62 of the absorbent core 14 may also include a substrate 72, a thermoplastic composition 73 on the substrate, an absorbent particulate polymer material 74 adhered to the second substrate 72 with the thermoplastic composition, and a thermoplastic composition 68 on the absorbent particulate polymer material 74 and at least a portion of the second substrate 72 or first layer of thermoplastic composition for immobilizing the absorbent particulate polymer material 74 on the second substrate 72. Although not illustrated, the second absorbent layer 62 may also include a cover layer such as the cover layer 70 illustrated in FIG. 4.

The substrate 64 of the first absorbent layer 60 may be referred to as a dusting layer and has a first surface 78 which faces the back sheet 20 of the diaper 10 and a second surface 80 which faces the absorbent particulate polymer material 66. Likewise, the substrate 72 of the second absorbent layer 62 may be referred to as a core cover and has a first surface 82 facing the top sheet 18 of the diaper 10 and a second surface 84 facing the absorbent particulate polymer material 74. The first and second substrates 64 and 72 may be adhered to one another with adhesive about the periphery to form an envelope about the absorbent particulate polymer materials 66 and 74 to hold the absorbent particulate polymer material 66 and 74 within the absorbent core 14.

According to a certain embodiment, the substrates 64 and 72 of the first and second absorbent layers 60 and 62 may be a non-woven material, such as those nonwoven materials described above. In certain embodiments, the non-wovens are porous and in one embodiment has a pore size of about 32 microns.

As illustrated in FIGS. 1-8, the absorbent particulate polymer material 66 and 74 may be deposited on the respective substrates 64 and 72 of the first and second absorbent layers 60 and 62 in small and large clusters 90 and 91 of particles to form a grid pattern 92 comprising land areas 94 and junction areas 96 between the land areas 94. The junction areas 96 in the grid pattern 92 contain little or no absorbent particulate polymer material 66 and 74. The land areas 94 and junction areas 96 can have a variety of shapes including, but not limited to, circular, oval, square, rectangular, triangular, and the like.

The small clusters 90 of absorbent particulate polymer material 66 and 74 are thinner than the large clusters 91 of absorbent particulate polymer material 66 and 74 and impart a lower basis weight of absorbent particulate polymer material 66 and 74 to the area of the absorbent core 14 in which the small clusters 90 are located. Likewise, the large clusters 91 of absorbent particulate polymer material 66 and 74 are thicker than the small clusters 90 of absorbent particulate polymer material 66 and 74 and impart a higher basis weight of absorbent particulate polymer material 66 and 74 to the area of the absorbent core 14 in which the large clusters 91 are located. This creates a varied profile of absorbent particulate polymer material across the absorbent core 14. At least one cavity can be created in the absorbent core by a combination of machine direction profiling and cross-machine direction profiling, so as to create at least one region having relatively little or no absorbent particulate polymer material (e.g., a low basis weight region) bounded by a region of relatively more absorbent particulate polymer material (i.e., a high basis weight region).

Figure 8:
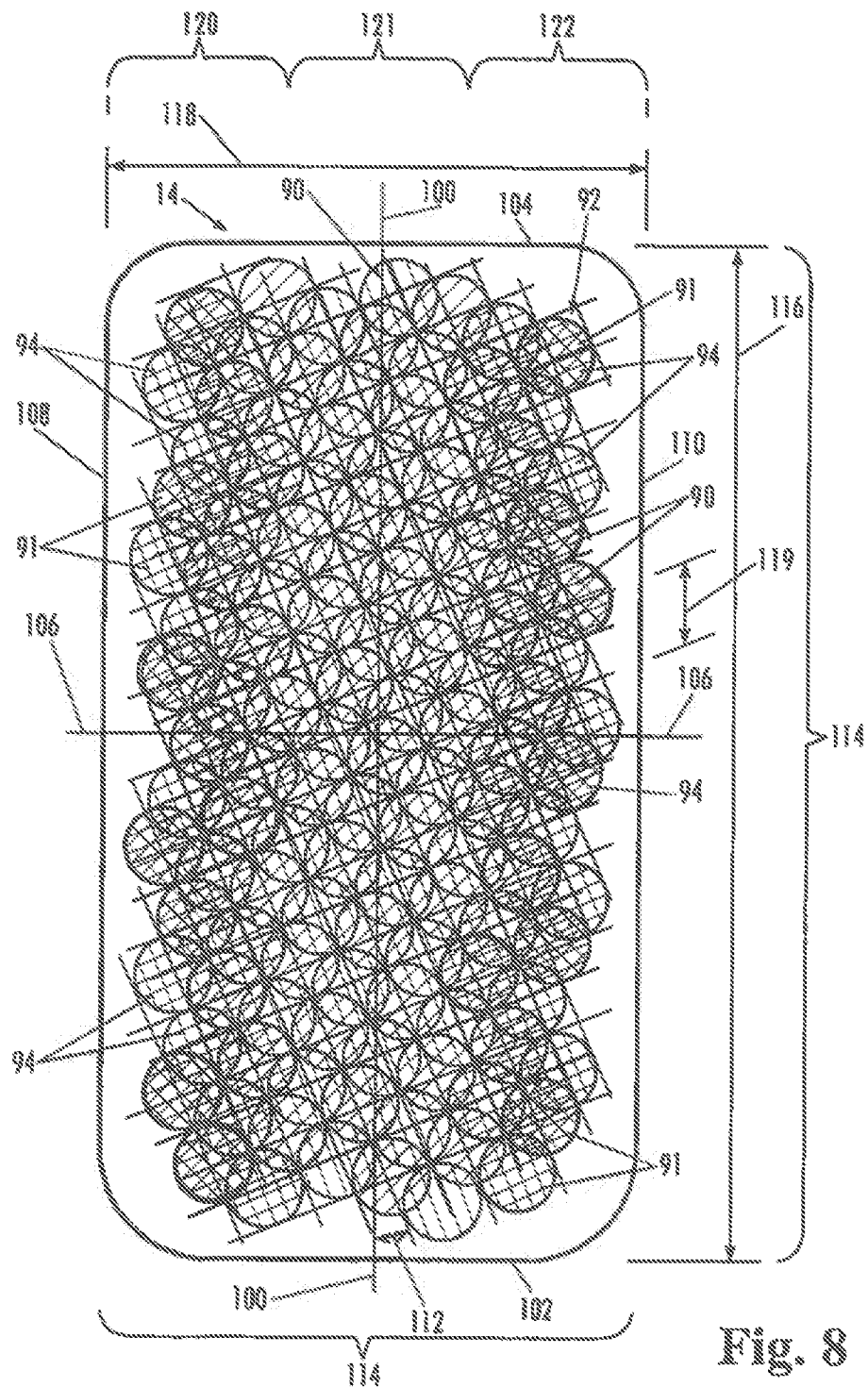
FIG. 8 is a plan view of the absorbent core illustrated in FIG. 7.

As shown in FIG. 8, the absorbent core 14 has a longitudinal axis 100 extending from a rear end 102 to a front end 104 and a transverse axis 106 perpendicular to the longitudinal axis 100 extending from a first edge 108 to a second edge 110. The grid pattern 92 of absorbent particulate polymer material clusters 90 and 91 is arranged on the substrates 64 and 72 of the respective absorbent layers 60 and 62 such that the grid pattern 92 formed by the arrangement of land areas 94 and junction areas 96 forms a pattern angle 112. While the pattern angle 112 may be such that the grid pattern 92 is parallel with the first and second edges 108 and 110 of the absorbent core 14, the pattern angle 112 may be greater than 0, or 15 to 30 degrees, or from about 5 to about 85 degrees, or from about 10 to about 60 degrees, or from about 15 to about 30 degrees from the longitudinal axis 100 of the absorbent core 14.

Figure 7:
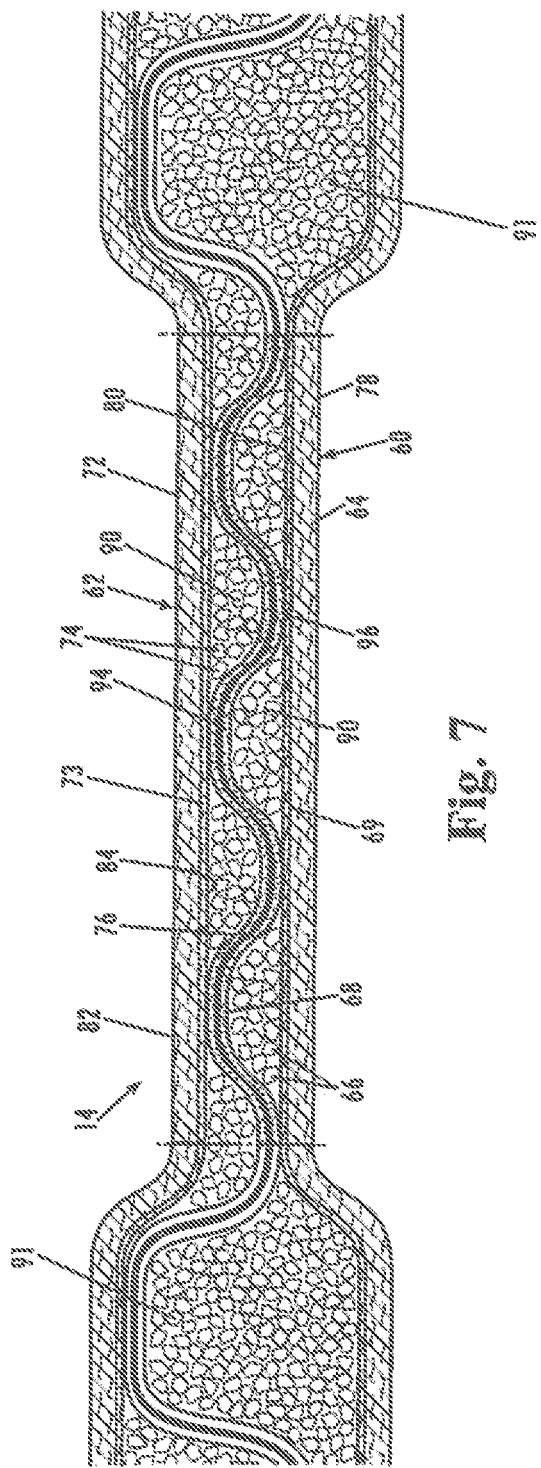
FIG. 7 is a partial sectional view of an absorbent core comprising a combination of the first and second absorbent core layers illustrated in FIGS. 5 and 6.

As best seen in FIGS. 7 and 8, the first and second layers 60 and 62 may be combined to form the absorbent core 14. The absorbent core 14 has an absorbent particulate polymer material area 114 bounded by a pattern length 116 and a pattern width 118. The extent and shape of the absorbent particulate polymer material area 114 may vary depending on the desired application of the absorbent core 14 and the particular absorbent article in which it may be incorporated. In a certain embodiment, however, the absorbent particulate polymer material area 114 may extend substantially entirely across the absorbent core 14, such as is illustrated in FIG. 8.

The size of the land areas 94 in the grid patterns 92 may vary. According to certain embodiments, the width of the land areas 94 in the grid patterns 92 ranges from about 8 mm to about 12 mm. In a certain embodiment, the width of the land areas 94 is about 10 mm. The junction areas 96, on the other hand, in certain embodiments, have a width or larger span of less than about 5 mm, less than about 3 mm, less than about 2 mm, less than about 1.5 mm, less than about 1 mm, or less than about 0.5 mm.

The first and second absorbent layers 60 and 62 may be combined together to form the absorbent core 14 such that the grid patterns 92 of the respective first and second absorbent layers 62 and 64 are offset from one another along the length and/or width of the absorbent core 14. The respective grid patterns 92 may be offset such that the absorbent particulate polymer material 66 and 74 is substantially continuously distributed across the absorbent particulate polymer area 114. In a certain embodiment, absorbent particulate polymer material 66 and 74 is substantially continuously distributed across the absorbent particulate polymer material area 114 despite the individual grid patterns 92 comprising absorbent particulate polymer material 66 and 74 discontinuously distributed across the first and second substrates 64 and 72 in clusters 90 and 91. In a certain embodiment, the grid patterns may be offset such that the land areas 94 of the first absorbent layer 60 face the junction areas 96 of the second absorbent layer 62 and the land areas of the second absorbent layer 62 face the junction areas 96 of the first absorbent layer 60. When the land areas 94 and junction areas 96 are appropriately sized and arranged, the resulting combination of absorbent particulate polymer material 66 and 74 is a substantially continuous layer of absorbent particular polymer material across the absorbent particulate polymer material area 114 of the absorbent core 14. In a certain embodiment, respective grid patterns 92 of the first and second absorbent layer 60 and 62 may be substantially the same.

In a certain embodiment as illustrated in FIGS. 1-8, the amount of absorbent particulate polymer material 66 and 74 may vary along the width 118 of the grid pattern 92 substantially perpendicularly to the longitudinal axis 36 of disposable absorbent diaper 10. In a certain embodiment, the grid pattern may be divided into absorbent zones 120, 121 and 122, or another number of zones, in which the amount of absorbent particulate polymer material 66 and 74 per unit area of the absorbent core 14 varies from zone to zone. The amount of absorbent particulate polymer material 66 and 74 may, in a certain embodiment, gradually transition from one of the plurality of absorbent zones 120, 121, and 122 to another. This gradual transition in amount of absorbent particulate polymer material 66 and 74 may reduce the possibility of cracks forming in the absorbent core 14.

In the embodiment illustrated in FIGS. 1-8 the first and second side absorbent zones 120 and 122 are spaced from one another and extend substantially parallel to the longitudinal axis 36 of the diaper 10 and the central absorbent zone 121 extends substantially along the longitudinal axis and between the first and second side absorbent zones 120 and 122. The absorbent particulate polymer material 66 and 74 present in the first and second side absorbent zones 120 and 122 of the absorbent core 14 has a basis weight greater than the basis weight of the absorbent particulate polymer material 66 and 74 present in the central absorbent zone 121 of the absorbent core 14.

In alternative embodiments, the absorbent particulate polymer material 66 and 74 in the central absorbent zone 121 of the absorbent core 14 has a higher basis weight than in the first and second side absorbent zones 120 and 122 of the absorbent core 14. When the absorbent core 14 according to this embodiment is subjected to a flush of liquid directed at the central absorbent zone 121, liquid that flows over and past the central absorbent zone 121 contacts the side absorbent zones 120 and 122. The first and second side absorbent zones 120 and 122 have more absorbent particulate polymer material and have greater capacity to absorb such liquid and deter flow of the liquid beyond the side absorbent zones 120 and 122 to prevent leakage.

Although the embodiment illustrated in FIGS. 1-8 has only three absorbent zones 120, 121, and 122, the absorbent diaper 10 may include any number of absorbent zones having varying basis weights of absorbent particulate polymer. Furthermore, in other embodiments, the absorbent particulate polymer material 66 and 74 may be varied in different patterns such as by placing more absorbent particulate polymer material in the central absorbent zone 121 than in the side absorbent zone 120 and 122 or alternating areas of greater and lesser amounts of absorbent particulate polymer material per unit area of the absorbent core.

Figure 9:
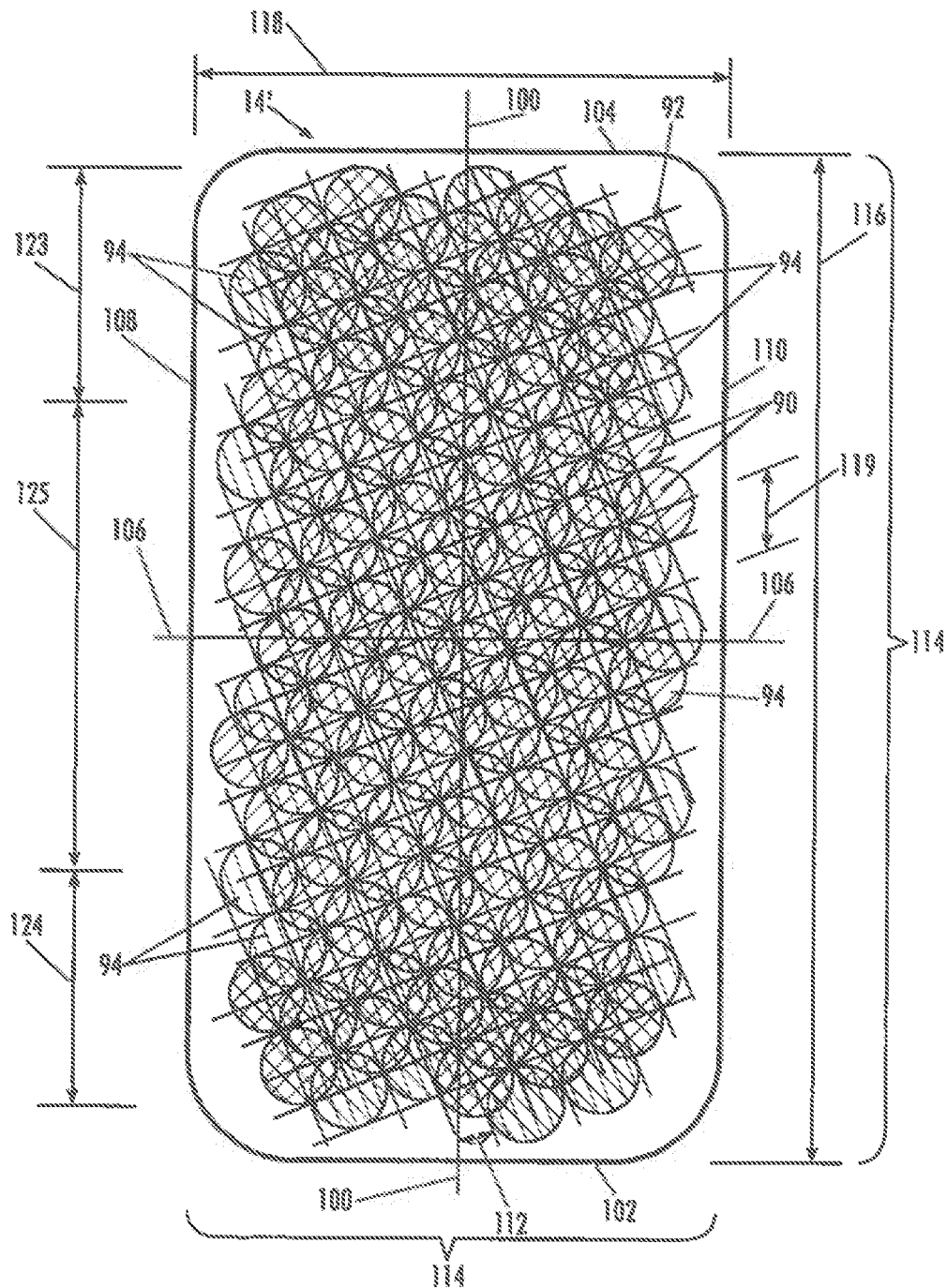
FIG. 9 is a plan view of an absorbent core wherein more absorbent particulate polymer material is present toward ends of the diaper than in a central zone of the diaper.

Another embodiment of an absorbent core 14' is illustrated in FIG. 9 and the basis weight of the absorbent particulate polymer material 66 and 74 varies across the absorbent core 14' in a direction substantially parallel to the longitudinal axis 36. This absorbent core 14' comprises first and second end absorbent zones 123 and 124, spaced form one another and extending substantially perpendicular to the longitudinal axis of the absorbent core, and a central absorbent zone 125, extending substantially along the longitudinal axis 36 and between the first and second end absorbent zones 123 and 124. The basis weight of the absorbent particulate polymer material in the absorbent end zones 123 and 124 of the absorbent core 14' is greater than in the central absorbent zone 125 of the absorbent core 14'. When the absorbent core 14' illustrated in FIG. 9 is subjected to a flush of liquid directed at the central absorbent zone 125, liquid that flows past the central absorbent zone 125 encounters end absorbent zones 123 and 124 which have greater capacity to absorb and hold such liquid.

Although the absorbent core 14' illustrated in FIG. 9 has only three absorbent zones 123, 124, and 125, the absorbent core 14' may include any number of absorbent zones arranged in a variety of different patterns of varying absorbent particulate polymer material basis weights. In other embodiments, the basis weight of the absorbent particulate polymer material 66 and 74 in the central absorbent zone 125 may be greater than in the end absorbent zones 123 and 124 or the absorbent core 14' may include a multitude of alternating absorbent zones of varying absorbent particulate polymer material basis weights.

Figure 10:
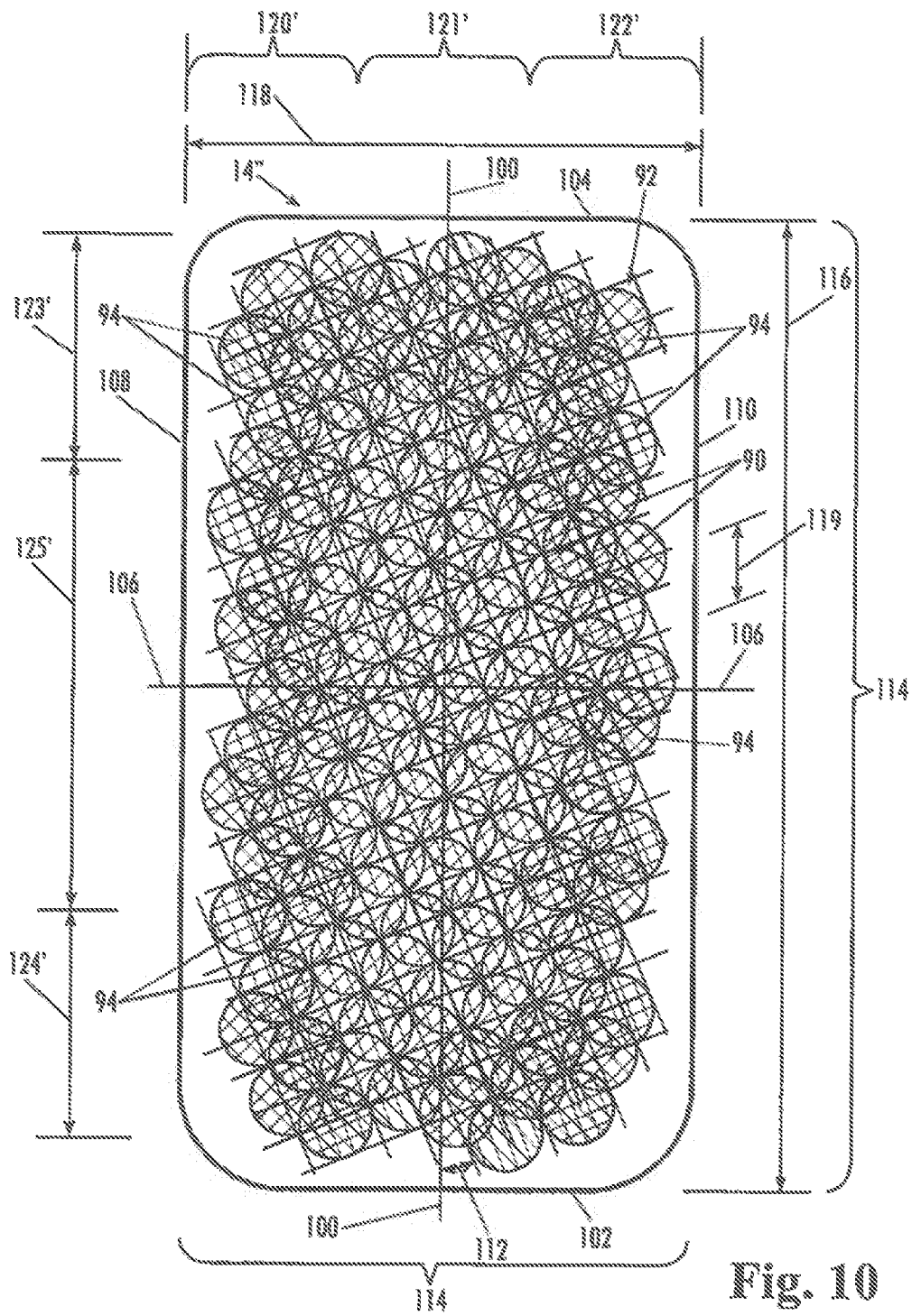
FIG. 10 is a plan view of an absorbent core wherein more absorbent particulate polymer material is present toward lateral edges and ends of the diaper than in a central zone of the diaper.

Another embodiment of an absorbent core 14" is illustrated in FIG. 10 and comprises first and second side absorbent zones 120' and 122' spaced from one another and extending substantially parallel to the longitudinal axis 36, first and second end absorption zones 123' and 124' spaced from one another and extending substantially perpendicularly to the longitudinal axis 36, and a central portion 121' and 125' extending substantially along the longitudinal axis 36 and between the first and second side absorbent zones 120' and 122' and between the first and second end absorbent zones 123' and 124'. The basis weight of the absorbent particulate polymer material 66 and 74 in the first and second side portions 120' and 122' of the absorbent core 14" is greater than the basis weight of the absorbent particulate polymer material 66 and 74 in the central portion 121' and 125' of the absorbent core 14" and the basis weight of the absorbent particulate polymer material 66 and 74 in the first and second end portions 123' and 124' of the absorbent core 14" is greater than the basis weight of the absorbent particulate polymer material 66 and 74 in the central portion 121' and 125' of the absorbent core 14". When the absorbent core 14" illustrated in FIG. 10 is subjected to a rush of liquid directed at the central absorbent zone 121' and 125', liquid that flows past the central absorbent zone 121' and 125' encounters and may be absorbed by the side absorbent zones 120' and 122' and the end absorbent zones 123' and 124' which all have greater absorbent particulate polymer material basis weights. As with the other embodiments described hereinabove, it should be understood that the absorbent particulate polymer material 66 and 74 may be arranged in a variety of different patterns of varying absorbent particulate polymer material basis weights. In one such embodiment, the central absorbent zone 121' and 125' may have a higher absorbent particulate polymer material basis weight than the side absorbent zones 120' and 122' and the end absorbent zones 123' and 124'.

Figure 11:
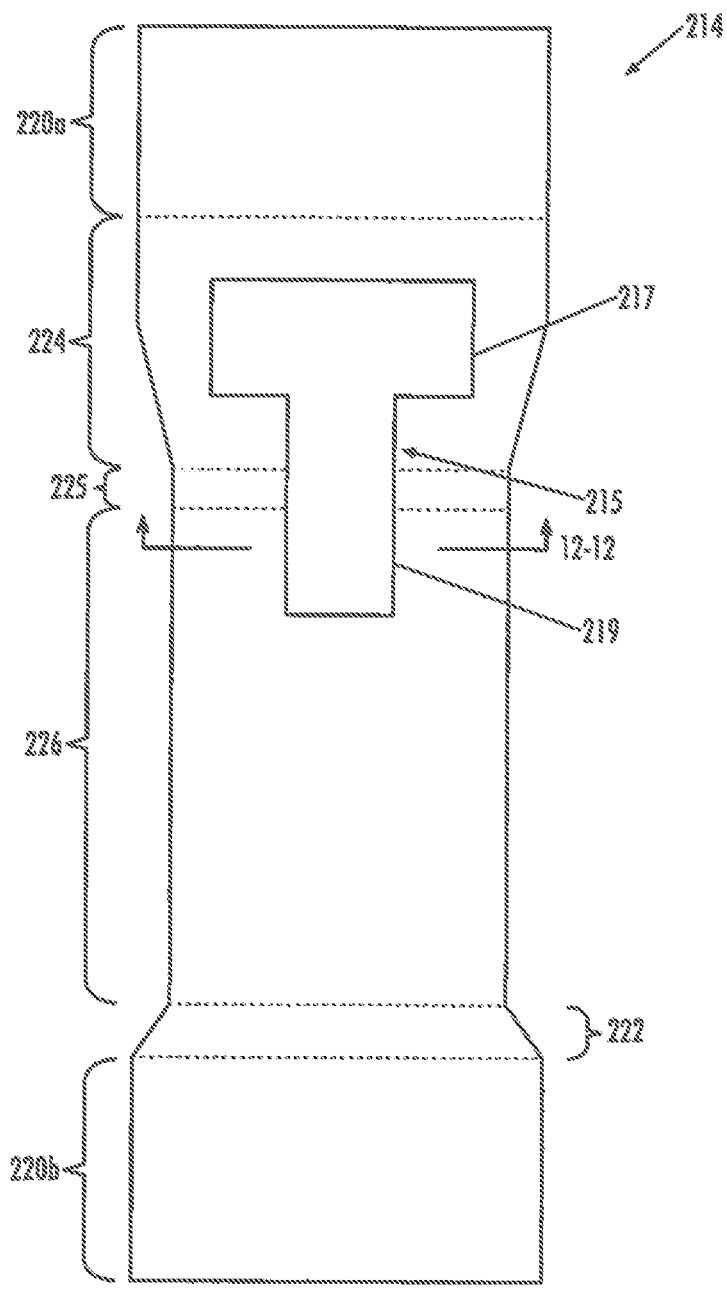
FIG. 11. is a plan view of an absorbent core in accordance with an embodiment of the present invention.
Figure 12:
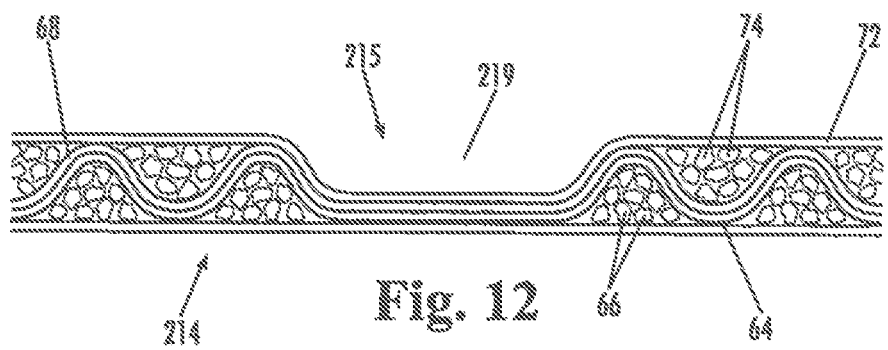
FIG. 12 is a cross-sectional view, taken along line 12-12 of the absorbent core illustrated in FIG. 11.

A certain embodiment of an absorbent core 214 is illustrated in FIGS. 11-12. Absorbent core 214 may be constructed like absorbent cores 14, 14', or 14" described herein. The absorbent core 214 comprises at least one cavity 215, which is sized and positioned to receive fecal matter, for example to contain and direct the fecal matter away from the skin of a person wearing a disposable absorbent article which comprises the absorbent core 214. In certain embodiments, the void volume of the cavity (or total volume of multiple cavities) may be from 2 ml to about 20 ml when the absorbent core 214 is in a dry state. When the absorbent core 214 becomes wet, expansion of the absorbent particulate polymer material 66 and 74 swells, causing the cavity volume to increase. For example, the void volume of the cavity may be from about 25 ml to 35 ml (in use, when fluid is present), e.g., about 30 ml. In one embodiment, the cavity volume may be from about 50 to about 70 ml when the absorbent core is in a saturated state.

The cavity may be defined at least about its perimeter by the absorbent particulate polymer material 66 and 74 (with associated first and second substrates 64 and 72 and thermoplastic material 68 and 76). For example, the cavity may be formed by CD and MD profiling of the core, creating an area with a lower basis weight absorbent particulate polymer material, or no absorbent particulate polymer material, as compared to surrounding areas of the absorbent core. Generally, the greater the basis weight difference between the regions, the greater the depth of the cavity. The volume of the cavity may increase upon swelling of the absorbent particulate polymer material, i.e., after at least one gush of liquid occurs and is taken up by the absorbent particulate polymer material.

Figure 28A:
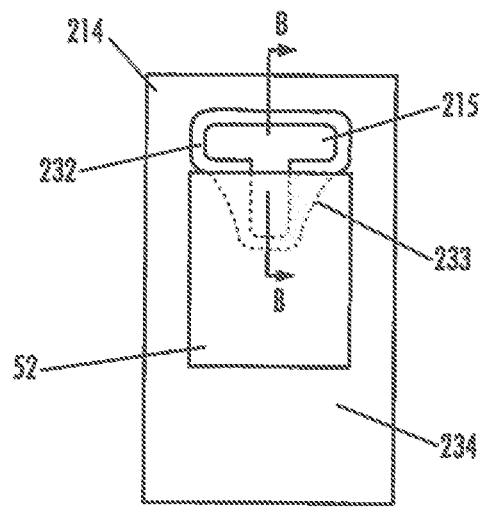
FIG. 28A is a plan view and FIG. 28B is a cross-sectional view, taken along sectional line B-B, of an absorbent core having a gradient of absorbent particulate polymer material around the cavity and an acquisition layer which augments the cavity, according to one embodiment of the invention.
Figure 28B:
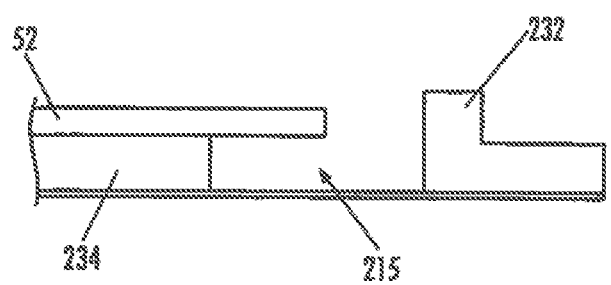

In a particular embodiment, the region defining the cavity may be substantially free of absorbent particulate polymer material 66 and 74. In one embodiment, the absorbent particulate polymer material that would have been located in the region of the cavity may be redistributed in the absorbent core in the region about the walls or perimeter of the cavity. In this way, the total capacity of the absorbent core is substantially maintained as compared to an absorbent core without such a cavity. One embodiment of such an absorbent core is illustrated in FIG. 28, as detailed below.

In one embodiment, the first channel of the cavity is located in the absorbent core along the central longitudinal axis of the diaper or pant at a position which is positioned at the so-called "poo point." That is, when the diaper or pant is worn by a wearer, the cavity will be in alignment with a predetermined region about the anus of the wearer. In one embodiment, the cavity is located about 10 mm from the anus position, which may work to direct the bowel movement into the cavity.

In a certain embodiment, the cavity 215 may include a first channel 219 elongated in a direction substantially parallel to and located about the central longitudinal axis 100, and (ii) a second channel 217 elongated in a direction substantially perpendicular to the central longitudinal axis 100. In one embodiment, the first and second channels of the cavity together may form a T-shape, as illustrated in FIG. 11. In other embodiments, the first and second channels of the cavity together may form a cross shape, or a Y-shape. The dimensions of the first channel generally should create a stable valley between the buttocks, yet provide a channel for fecal matter; if too wide then the first channel loses stability and if too narrow then it does not adequately accommodate the bowel movement. In various embodiments, the first channel 219 of the cavity 215 may have a width from about 10 mm to about 40 mm and a length from about 10 mm to about 130 mm. In one example, the first channel 219 of the cavity 215 may have a width of about 20 mm and may have a length of about 70 mm. The second channel generally should be dimensioned to provide distribution of the bowel movement in the cross direction once it has been directed to the back of the diaper. In other various embodiments, the second channel 217 of the cavity 215 may have a width from about 10 mm to about 40 mm and a length from about 10 mm to about 100 mm. In another example, the second channel of the cavity may have a width of about 30 mm and a length of about 50 mm. In this T-shaped cavity embodiment, channel length refers to dimensions in the machine direction, and channel width refers to dimensions in the cross-machine direction.

Figure 24:
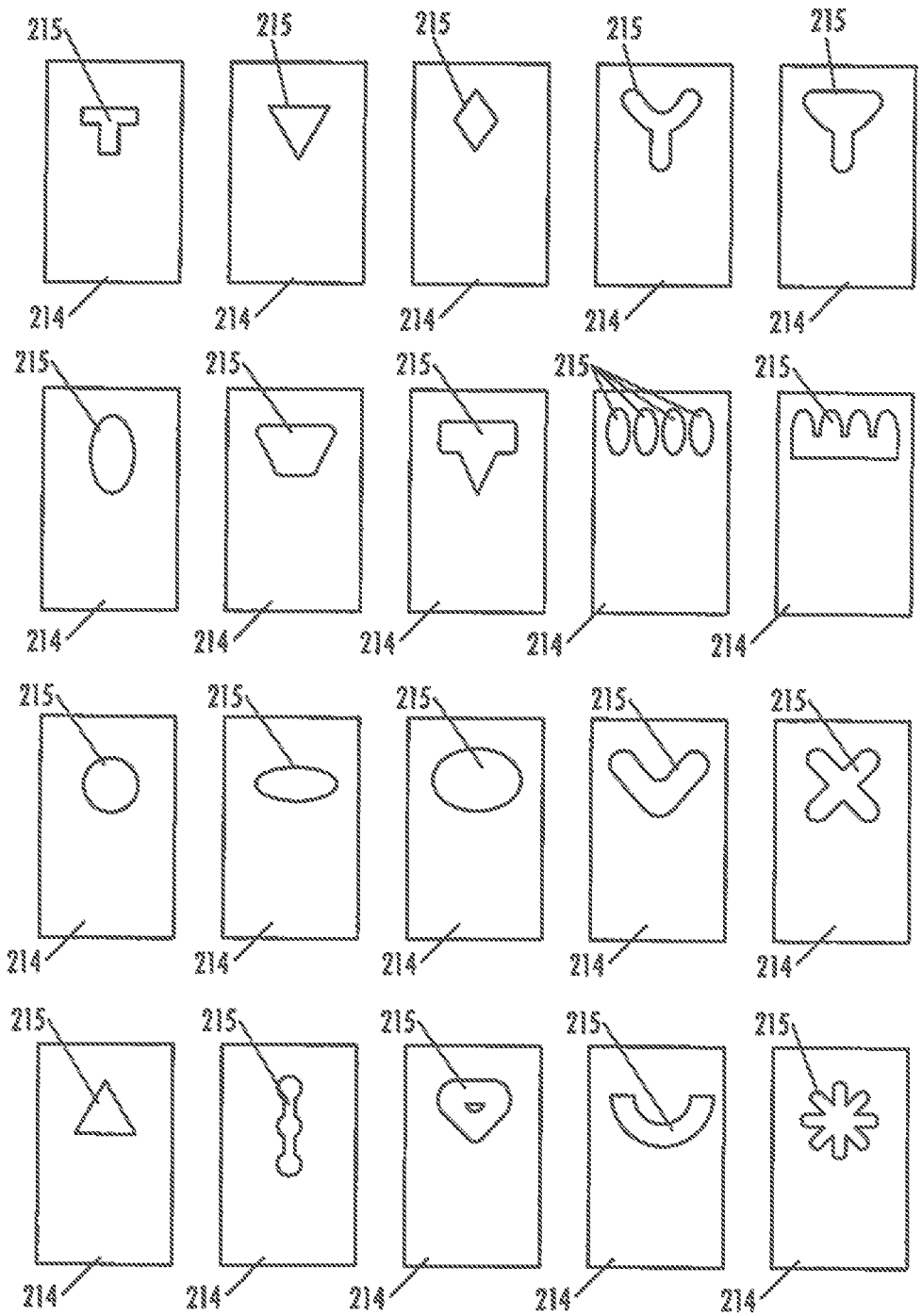
FIG. 24 shows plan views of twenty different absorbent cores with different possible geometric designs of cavities, according to certain embodiments of the invention.

The one or more cavities in the absorbent core may have a variety of different geometric shapes. Combinations of different geometric shapes may be used together. The shapes may be connected or may be discrete from one another. The cavities generally are sized and located in the absorbent core in a position to facilitate reception and storage of body exudates, such as fecal matter. The shapes generally may straddle the longitudinal axis. FIG. 24 illustrates various examples of possible shapes and designs of cavities 215 in the absorbent core 214, including T-shaped, triangular, diamond, Y-shaped, combination of semi-circle and rectangle, oval, trapezoidal, combination of rectangle and triangle, array of discrete rectangles, array of rectangles connected with perpendicular bar, circular elliptical, V-shaped, X-shaped, triangular, array of circles connected with bar, interrupted triangular, U-shaped, and star-shaped.

In addition to the basis weight variation, e.g., the CD and MD profiling, to define the at least one cavity of the absorbent core, the absorbent particulate polymer material present in the remaining part of the absorbent core (other than the at least one cavity) may have a basis weight that varies across other areas of the absorbent core in a direction substantially perpendicular to the central longitudinal axis, in a direction substantially parallel to the central longitudinal axis, or in both directions. Generally, the absorbent particulate polymer material is redistributed away from the cavity area, so that the liquid loading capacity is substantially maintained (versus a conventional flat absorbent core). In one embodiment, illustrated with reference to FIG. 11, the absorbent core 214 includes back end and front end absorbent zones 220$a$ and 220$b$, respectively. The cavity 215 is defined in and bounded by central absorbent zones 226 and 224, and rear transitional absorbent zone 225 disposed therebetween. The central absorbent zone 226 and front end absorbent zone 220$b$ front end have a front transitional zone 222 disposed therebetween.

In an embodiment, the basis weight of absorbent particulate polymer material in back end and front end absorbent zones 220$a$ and 220$b$ is from about 200 g/cm$^2$ to about 300 g/cm$^2$, for example between about 220 g/cm$^2$ and 250 g/cm$^2$, such as about 233 g/cm$^2$. In an embodiment, the basis weight of absorbent particulate polymer material in central absorbent zone 224 is from about 450 g/cm$^2$ to about 650 g/cm$^2$, for example, between about 530 g/cm² and 600 g/cm², such as about 568 g/cm². In an embodiment, the basis weight of absorbent particulate polymer material in central absorbent zones 226 is from about 200 g/cm² to about 400 g/cm², for example, between about 250 g/cm² and 350 g/cm², such as about 284 g/cm². In an embodiment, the rear transitional absorbent zone 225 has a basis weight of absorbent particulate polymer material between about 300 g/cm² and 400 g/cm², such as about 333 g/cm². In an embodiment, the front transitional absorbent zone 222 has a basis weight of absorbent particulate polymer material between about 200 g/cm² and 300 g/cm², for example between about 240 g/cm² and 280 g/cm². Transition zones are optional, and each transition zone may comprise further gradation within the transition zone.

The absorbent core 214 may comprise a core cover 72 and a dusting layer 64 adhered to one another about the periphery of the absorbent core 214 to form an envelope about the absorbent particulate polymer materials 66/74 to hold the absorbent particulate polymer material within the absorbent core 214.

Figure 25A:
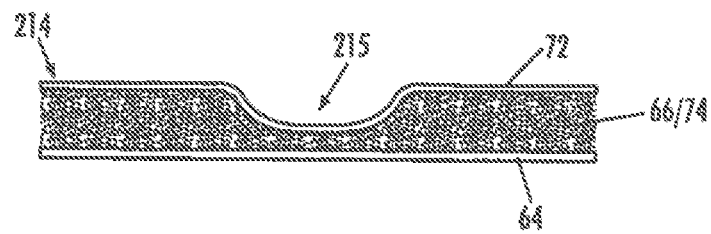
FIGS. 25A-C are cross-sectional views of various constructions of a cavity in an absorbent core, according to certain embodiments of the invention.
Figure 25B:
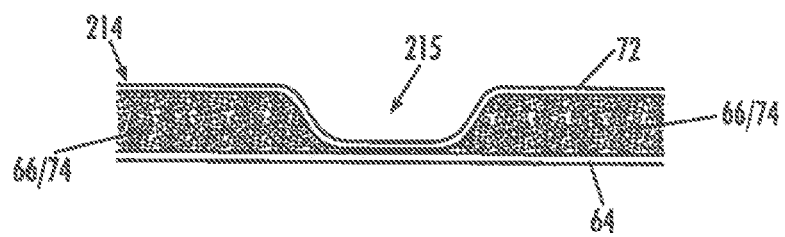

The cavity may be formed with various constructions. For example, FIG. 25A illustrates one embodiment in which some of the absorbent particulate polymer materials 66/74 is present in the cavity 215, but at a lower basis weight relative to the surrounding region of the absorbent core 214. In another embodiment, as illustrated in FIG. 25B, substantially none of the absorbent particulate polymer materials 66/74 is present in the cavity 215.

Figure 25C:
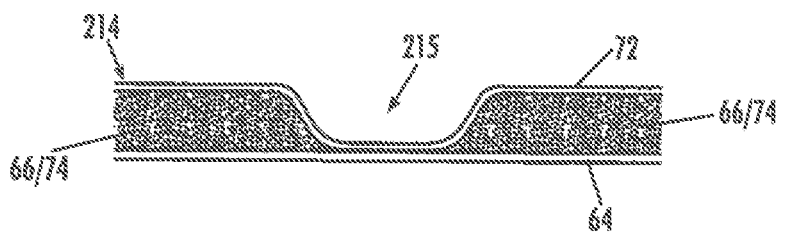

In a particular embodiment, the core cover 72 and the dusting layer 64 may be adhered to one another about an area defining the bottom of the at least one cavity 215, as illustrated in FIG. 25C. In this embodiment, there is no absorbent particulate polymer material in the bottom of the cavity; however, the sidewalls of the cavity are still defined by the absorbent particulate polymer material. This embodiment may aid cavity shape/volume retention when the absorbent particulate polymer materials swells and takes additional volume, as it would be undesirable for the absorbent particulate polymer materials to swell and thereby reduce the cavity volume available for receiving and holding a bowel movement. In a certain sub-embodiment, most or all of layers of the absorbent article construction about the cavity are connected to the dusting layer, in order to sustain the cavity. These layers can be glued or bonded by application of heat and/or pressure.

In one embodiment, the disposable absorbent article 10 may further include an acquisition system 50 located between the absorbent core 214 and the top sheet 18. In one embodiment, the acquisition system 50 may include an upper acquisition layer 52, which faces the top sheet 18, and a lower acquisition layer 54, which faces the absorbent core 214. The upper acquisition layer 52 may or may not cover the at least one cavity 215. The lower acquisition layer 54 may or may not cover the at least one cavity 215. In another embodiment, the lower acquisition layer may be omitted. Various constructions of absorbent core and acquisition layers are possible; examples are illustrated in FIGS. 26-28.

Figure 26A:
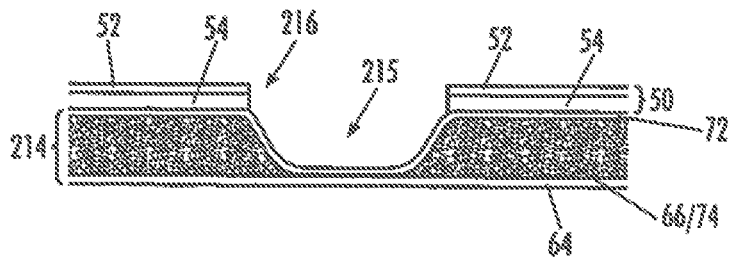
FIGS. 26A-C are cross-sectional views (FIGS. 26A-B) and a plan view (FIG. 26C) of various constructions of a cavity defined, at least in part, by an acquisition system, according to another embodiment of the invention.
Figure 26B:
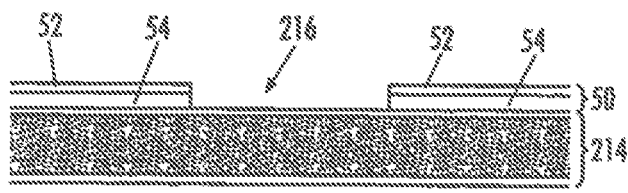
Figure 26C:
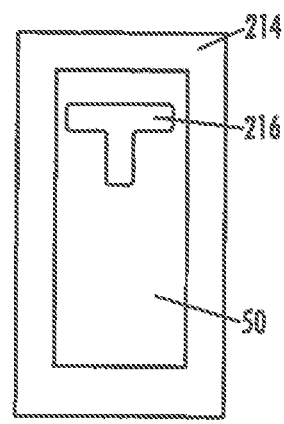

In one embodiment, the at least one cavity 215 may further be defined about its perimeter by interior edges of an aperture 216 in the acquisition system 50 and absorbent core 214, as illustrated in FIG. 26A. In an alternative embodiment, the absorbent core is substantially planar and the cavity is defined substantially by interior edges of an aperture 216 in the acquisition system 50, as illustrated in FIGS. 26B-C. In this embodiment, the void volume achieved is a function of the thickness of the acquisition system. In one embodiment, the aperture 216 in the acquisition system 50, which defines the shape of the cavity, may be made by a stamping process, adapted from stamping equipment and processes known in the art. The borders of the acquisition layer may be sealed.

FIGS. 27A-E illustrate some of the possible configurations of the acquisition system 50 and absorbent core 214. In FIG. 27A, the cavity 215 is not covered at all by the acquisition system 50, which is offset toward the front end of the absorbent core (e.g., toward the pee point). In FIG. 27B, the cavity 215 is partially covered by the acquisition system 50. In FIG. 27C, the cavity 215 is completely covered by the acquisition system 50. In FIG. 27D, a majority of the (smaller) acquisition system 50 is positioned over the cavity 215. In FIG. 27E, the acquisition system 50 is shaped to surround part of, but not cover, the cavity 215.

The upper and lower acquisition layers 52 and 54 may, but need not, cover identical areas of the absorbent core 214. In various embodiments, the upper and lower acquisition layers 52 and 54 may have different sizes and/or positions relative to the absorbent core. In FIG. 27F, the upper acquisition layer 52 covers part of the cavity 215, and the lower acquisition layer 54 covers none of the cavity. In FIG. 27G, the upper acquisition layer 52 covers part of the cavity 215, and the lower acquisition layer 54 is shaped to surround part of but not cover the cavity 215. In FIG. 27H, the upper acquisition layer 52 covers all of the cavity 215, and the lower acquisition layer 54 is shaped to surround part of but not cover the cavity 215. In FIG. 27I, the upper and lower acquisition layers 52 and 54 are approximately coextensive and include an aperture surrounding all of the cavity 215 in the absorbent core 214. In FIG. 27J, the upper acquisition layer 52 covers all of the cavity 215, and the lower acquisition layer 54, which is smaller than the upper acquisition layer 52 and does not cover the cavity 215. In FIG. 27K, the cavity 215 is covered by a single (upper) acquisition layer 52.

In another alternative embodiment, an absorbent core is provided with a cavity that is a through hole extending all the way through the core cover, absorbent particulate polymer materials, and dusting layer. For instance the cavity may be formed by a stamping process, and then the borders/edges of the cavity may be sealed, for example, by use of an adhesive and/or a heating or pressure process. In such an embodiment, the back sheet, and/or another layer, of the absorbent article may serve as the back/bottom of the cavity to contain the bowel movement.

The acquisition system may augment the caliper of the cavity of the absorbent article. In one embodiment, shown in FIGS. 28A-B, the absorbent core 214 includes a cavity 215, which is partially covered by an acquisition layer 52. The basis weight (and thickness) of the absorbent particulate polymer material in the absorbent core 214 varies in the regions about the cavity 215. The basis weight in region 232 is higher than the basis weight in region 234. Region 233 may provide a smooth gradient of basis weight between regions 232 and 234. The acquisition layer 52 may supplement the caliper of region 234 to approach, meet, or exceed the caliper of region 232.

Figure 13:
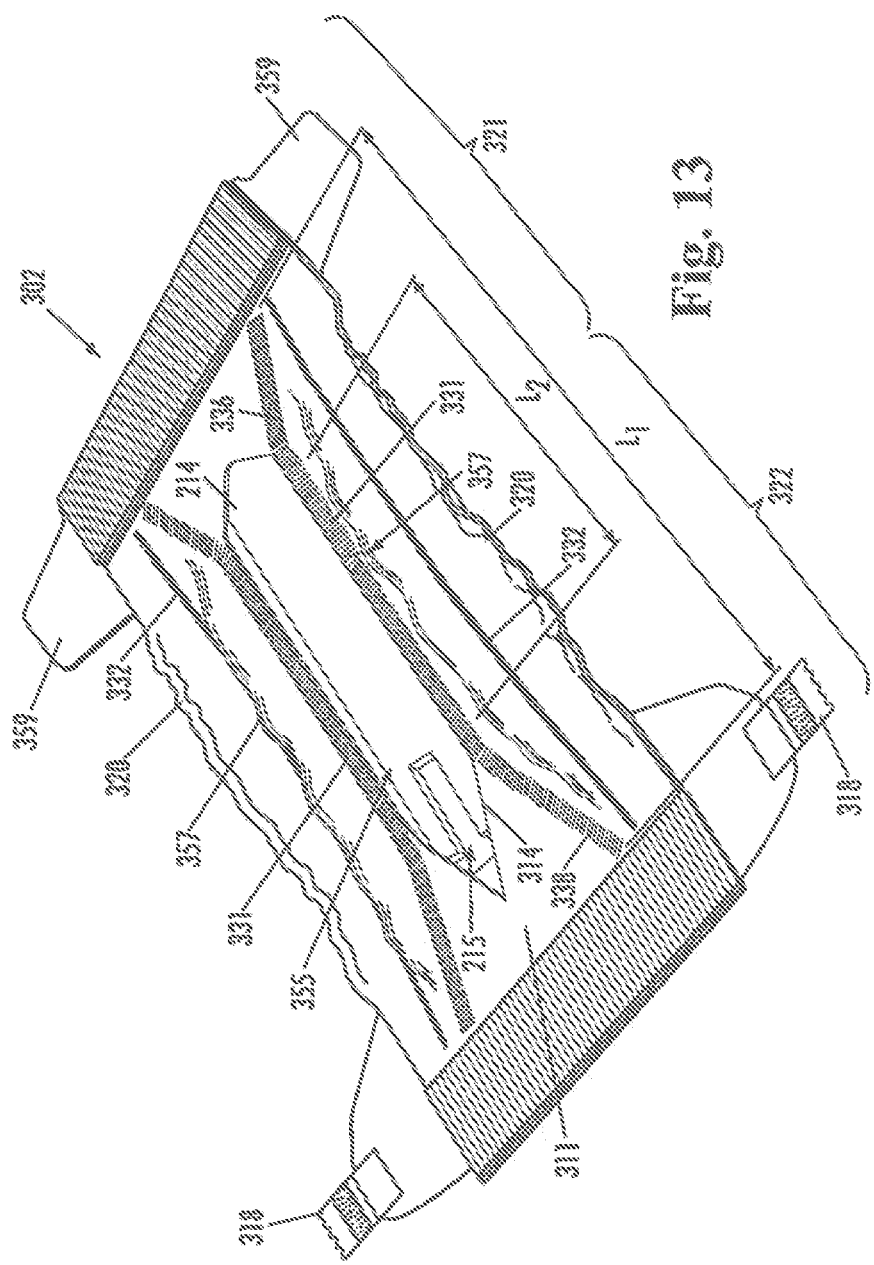
FIG. 13 is a perspective view of an absorbent article in accordance with an embodiment of the present invention, including an elasticized top sheet having an opening for receiving fecal matter.
Figure 14:
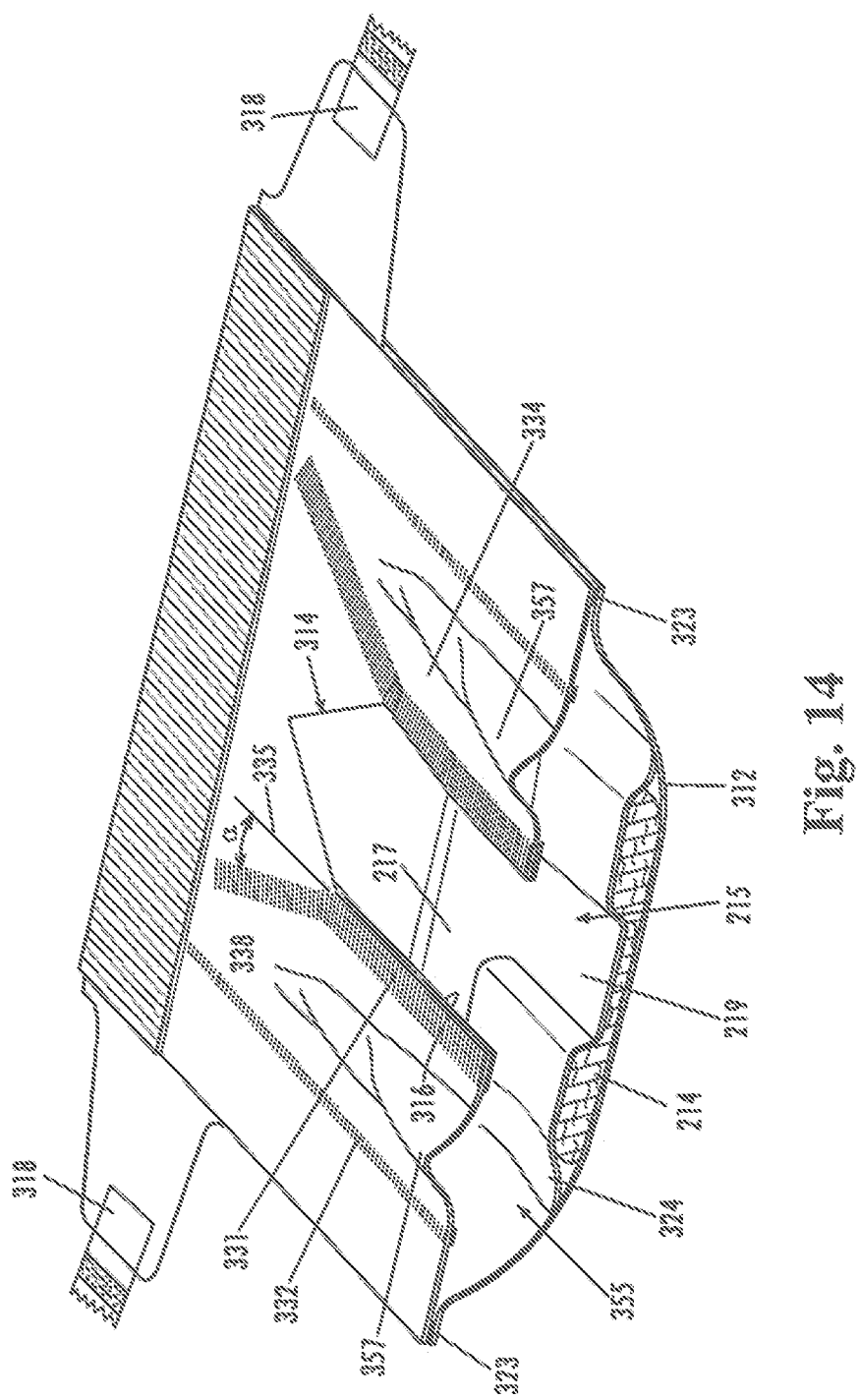
FIG. 14 is a cross-sectional, perspective view of the absorbent article illustrated in FIG. 13.
Figure 15:
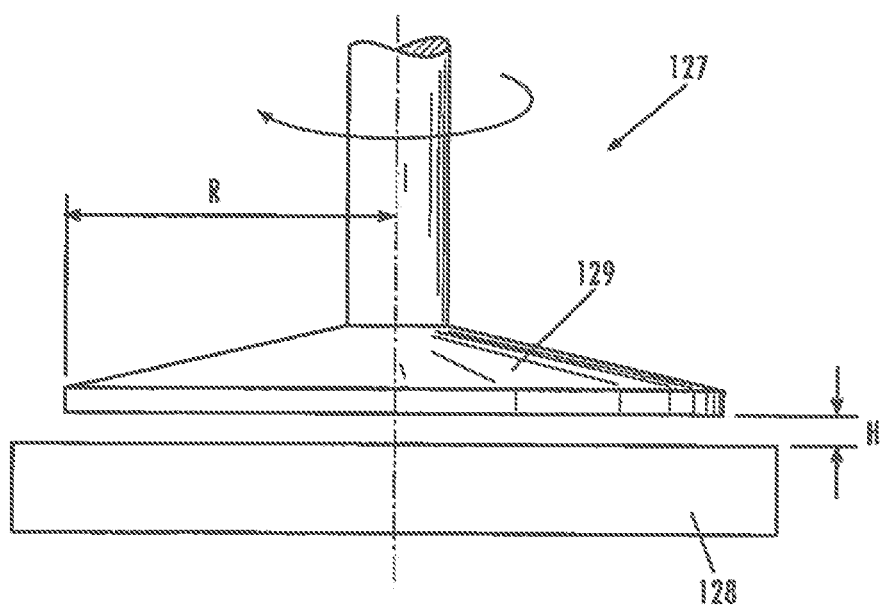
FIG. 15 is a schematic representation of a rheometer.

In another embodiment, which is illustrated in FIGS. 13 and 14, an absorbent core 214 is part of a disposable absorbent article 302 that comprises an elasticized top sheet 311, which includes an opening 314 and that in use forms a void 355 for fecal matter encapsulation. This opening 314 is an area completely circumscribed by the top sheet 311, but where the top sheet material is not present, and which is large enough to receive fecal material, for example, being at least 2 cm long or wide, or having a surface area of at least 2 cm². In a certain embodiment, the elasticized top sheet 314 generally is located adjacent the cavity 215, such that at least a portion of the opening 314 may be substantially aligned with the first channel 219 of the cavity 215 in the absorbent core 214.

The top sheet 311 and the opening 314 each have a front region 321 and a back region 322. The diaper 302, illustrated in FIGS. 13-14, includes a back waist band with ears with fasteners 318 and a front waist band 359 with receiving areas for the fasteners. In some configurations, the fasteners comprise hooks and/or adhesive and the receiving areas may be formed from loop-containing material. The diaper 302 further may include elasticated bands along the longitudinal side edges of the diaper 302, so called leg cuffs 320. Leg cuffs may also be referred to as leg bands, side flaps, barrier cuffs, or elastic cuffs, as described in; U.S. Pat. Nos. 3,860,003; 4,808,178 and 4,909,803; 4,695,278 and 4,795,454.

The disposable absorbent article 302 may also include a sub-layer (which may be part of the absorbent core) disposed between the top sheet 311 and the absorbent core 214, capable of accepting, and/or immobilizing bodily exudates, typically fecal material. For example as shown in FIG. 14, the absorbent core 214 may comprise a specific sub-layer 324, which comprises means to immobilize fecal material, for example, a layer with vertically extending (z-direction) fibers, or an apertured web or film, as described herein. Suitable materials for use as the sub-layer may include large cell open foams, macro-porous compression resistant non woven highlofts, large size particulate forms of open and closed cell foams (macro and/or microporous), highloft non-wovens, polyolefin, polystyrene, polyurethane foams or particles, structures comprising a multiplicity of vertically oriented, which may be looped, strands of fibers, and/or apertured formed films. (As used herein, the term "microporous" refers to materials that are capable of transporting fluids by capillary action, but having a mean pore size of more than 50 microns. The term "macroporous" refers to materials having pores too large to effect capillary transport of fluid, generally having pores greater than about 0.5 mm (mean) in diameter and more specifically, having pores greater than about 1.0 mm (mean) in diameter, but typically less than 10 mm or even less than 6 mm (mean).

The top sheet 311 with at least one opening 314 may be made as described in U.S. Patent Application Publication No. 2007/0197992 A1 to Martynus et al., which is incorporated herein by reference. The top sheet may further comprise, in one embodiment, a genital coversheet as described in the same published application.

The exact shape of the opening 314 may vary, depending on the size of the top sheet 311 and/or the absorbent article 302. For example, in one embodiment the opening is in the form of a slit opening with substantially parallel longitudinal side edges, which are connected in the front and back by V-shaped or rounded V-shaped, as shown in FIG. 13, front and back edges, wherein both the front and back V-shaped edges comprise two angled edges. In some embodiments, the back V-shaped edges may have a larger angle than the front V-shaped edges. The front V-shaped edges may have an angle of 20° to 100° or, alternately, from 45° to 65°, as shown in FIG. 14. The slit opening may optionally extend into an additional cut-out area which is, for example, diamond shaped. In an embodiment, best illustrated in FIG. 14, the opening 314 comprises a front end portion 336, which is curved, disposed between longitudinal side edges 316 of the opening.

The dimensions the opening 314 may also vary, depending on the size of the top sheet 311 and/or the absorbent article 302. In some embodiments, the top sheet 311 may have a slit opening having a longitudinal dimension (length) substantially parallel to the longitudinal axis of the top sheet 311 and of the diaper 302. In a stretched state, the opening 314 (or openings) of the top sheet may be configured such that from 20% to 40% or from 20% to 30% of the length of the opening (or total length of the openings) extends from the transverse axis of the top sheet toward the front edge of the top sheet, and the remaining percentage extends towards the back edge of the top sheet. In some embodiments, the maximum length of the slit opening may be about 40% to 90%, about 50% to 80%, or about 60% to 70% of the total length L of the absorbent article. In one example, a size 4 diaper may have a maximum top sheet length of between 45 cm and 55 cm or between 48 cm and 52 cm. In some embodiments, the length of the single slit opening, when the diaper is in stretched state, may be from 20 cm to 40 cm; from 25 cm to 35 cm; or from 28 cm to 32 cm. In some embodiments, the average width of the opening, in stretched state, may be from 5% to 30% or 10% to 25% of the average width of the top sheet (including opening width). In one example, a size 4 diaper may have an average width of the opening of from 15 mm to 60 mm or from 20 mm to 40 mm.

As shown in FIG. 13, the top sheet 311 may include a primary elasticated area 331 adjacent to or in close proximity with each longitudinal side edge 316 of the opening 314 to form a pair of opposing, elasticated areas. In some embodiments, the primary elasticated areas may extend from the side edges 316 of the opening 314 towards or completely to the front and back edge of the top sheet 311. Thus, the primary elasticated areas may be longer than the opening 314. The elasticated area may be positioned over the full length of the top sheet, or at least the part of the top sheet which in use is intended to receive body exudates (e.g., the top sheet minus the parts thereof which form (part of) the waist bands). An elasticated area in the top sheet may be formed from a multitude of thin strands of elastic material or, for example, from a single band of elastic material. The absorbent article may also include secondary elasticated areas in each crotch side portion (i.e., the portion of the top sheet between the longitudinal side edge of the top sheet 311 and the longitudinal side edge of the opening 314). Each secondary elasticated area may have an overall curvature, curving away from the primary elasticated area of the same crotch side portion.

As shown in FIG. 13, the primary elasticated areas 331 may be positioned along the longitudinal side edges 316 of the opening 314. The top sheet 311 may also have secondary elasticated areas 332, or even tertiary elasticated areas (not shown). The primary elasticated areas 331 have each a central region with a length $L_2$, the central regions being substantially parallel to one another, whereby $L_2$ may be about 30% to 70% of the total length $L_1$ of the primary elasticated areas 331. In an embodiment, $L_2$ is about 40% to 80% of the maximum length of the opening 314. The primary elasticated areas 331 may have an X-shape, whereby the front end portions 336 bend away from one another and the back end portions 338 bend away from one another. The primary elasticated areas may also be parallel, such as described in EP Application Publication EP-A-1201212.

The primary elasticated area may be shaped such that it has a central portion that is substantially parallel to the central portion of the opposing primary elasticated area. In an embodiment, the central portion has a length $L_2$ which may be 30% to 70% of the total length $L_1$ of a corresponding elasticated area, and may be about 40% to 80% of the maximum length of the opening. In some embodiments, the total length of the elasticated area may be about 70% to 90%, about 80% to 90%, or about 85% of maximum length of the top sheet 311. The length of the primary elasticated area may also depend on the size of the top sheet 311 and/or the article 302. For example, for a size 4 diaper as described above the average length of the elasticated area in stretched state, may be at least 35 cm, or from 35 cm to 45 cm. The width of the elasticated areas on the top sheet may also vary, depending on the exact dimensions of the top sheet 311 and/or the article 302. For example, for size 4 diapers as described above, a primary elasticated area, in stretched state, may be an elastic band, or a multitude of elastic strands, that has an average width of about 3 mm to 50 mm, about 3 mm to 40 mm, about 3 mm to 20 mm, or about 5 mm to 20 mm.

The front end portions of two opposing primary elasticated areas may bend away from one another (in the plane of the top sheet), so that the distance between the end edges of the opposing front end portions of two opposing elastic areas is larger than the distance between the central portions of two opposing elastic areas, and equally, the distance between the end edges of the opposing back end portions of two opposing elastic areas is larger that the distance between the central portions of two opposing elastic areas. For example, as shown in FIG. 14, the primary elasticated areas 331 may be in the shape of an X, whereby each front end portion 336 of the elasticated area has an angle α with the longitudinal line 335 parallel to the longitudinal axis of the top sheet 311 and through that part of the elasticated area that is (directly) adjacent a longitudinal side edge 316 of the opening. In one embodiment, this angle α may be about 17° to 30° in stretched state. In one embodiment, each back end portion 338 of the elasticated area also may have an angle which may be about 17° to 30° in stretched state.

In some embodiments, the front end portion of a primary elasticated area may have an angle with a longitudinal line through the central portion of the elasticated area and parallel to the longitudinal axis of the top sheet, the angle may be between 10° and 40°, between 17° to 35°, or between 20° and 35°. In other embodiments, the back end portion of each of the primary elasticated areas may have an angle with a longitudinal line through the central portion of the elasticated area and parallel to the longitudinal axis of the top sheet. In some embodiments, the angle may be between 10° and 40°, between 17° to 35°, or between 20° and 35°. When both front end portions and both back end portions have an angle as above, the primary elasticated areas have, as is herein referred to, an X-shape, and a suitable X-shape is exemplified in FIG. 13.

In some embodiments, the front end and/or the back end and/or the central portion of an elasticated area may be curved rather than straight. In such an embodiment, the angles above may be determined by the angle of the tangent line through the center point of the front end and/or back end, with the line parallel to the longitudinal axis of the top sheet and tangent to the center point of the central portion of the elasticated area.

The elasticated areas herein may be formed by attaching an elasticated material in stretched state or in a partial stretched state to the top sheet or to one or more carrier materials that are then subsequently attached to the top sheet. The elastic materials may be in the form of a multitude of strands or a single band with an average thickness (e.g., gauge) of at least 20 microns, at least 40 microns, or at least 60 microns. In some embodiments, the elastic material has an average thickness up to about 300 microns, up to 200 microns, or up to 150 microns. Suitable materials may have an average thickness of about 70 to 100 microns. Suitable elastic materials used herein may include VFE-CD, available from Tredegar, and L-86, L-89, or L-90, available from Fulflex (Limerick, Ireland).

The absorbent article 302 may be sag-tolerable and may include a top sheet 311 that is sag-tolerable. This means that the top sheet does not sag when the back sheet and absorbent core sag due to increased weight of the body exudates received by the article. In addition, the top sheet keeps its z-direction alignment with the anal region and genitals of the wearer, and may also keep its x and y direction alignment. The absorbent article (e.g., diaper or training pants) may include a means to ensure that the top sheet stays in about the same contact or close proximity with the wearer's anal and/or genital region when the back sheet and core sag, compared to just after application of the article to the wearer, when the back sheet and core do not yet sag. In some embodiments, the top sheet is sag-tolerable such that when the geometrical center point of the back sheet is pulled down 4 cm, (i) the top sheet does not move down more than 0.5 cm, more than 0.25 cm, or does not move down at all, and/or (ii) the longitudinal side edges of the opening do not move in the x and y direction more than 0.5 cm, more than 0.25 cm, or do not move at all.

In some embodiments, the top sheet 311 may be sag-tolerable and thereto non-elastically extendable and may have thereto one or more transverse folds and/or longitudinal folds 357, as shown in FIGS. 13-14, in a non-elasticated area 334. In some configurations, the average width of the top sheet 311, including the width of the opening 314, may be larger than the average distance between the longitudinal attachment areas of the top sheet 311 to the back sheet 312. In other configurations, the average width of the top sheet, including the width of the opening, may be larger than the average width of the back sheet. As such, the top sheet may, for example, have one or more transverse and/or longitudinal folds, which can unfold in use and allow sagging of the core and back sheet, while the top sheet remains in place. In some embodiments, the top sheet 311 with the longitudinal folds 357 is not attached to the absorbent core 214, but directly to the back sheet 312 with longitudinal attachment lines 323, to ensure that the diaper 302 and the top sheet 311 thereof are sag-tolerable.

In one embodiment, the absorbent article 10 may include one more top sheets that facilitate passage of bowel movement through the top sheets and into the at least one cavity 215. Examples of such top sheets are described in U.S. Patent Application Publication No. 2004/0092900, U.S. Pat. No. 5,342,338, European Patent Application Publication No. 1201212. As described in U.S. Pat. No. 5,342,338 to Roe, the absorbent article 10 may include a first top sheet with apertures large enough for low-viscosity fecal material to pass through it.

The amount of absorbent particulate polymer material 66 and 74 present in the absorbent core 14 (or 214) may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In a particular embodiment, the absorbent core 14 (or 214) consists essentially of the first and second substrates 64 and 72, the absorbent particulate polymer material 66 and 74, and the thermoplastic adhesive composition 68 and 76. In an embodiment, the absorbent core 14 (or 214) may be substantially cellulose free.

In certain embodiments which are not substantially cellulose free, the absorbent core 14 (or 214) can include some amount of cellulosic fiber material, such as airfelt. A relatively low amount of cellulosic material is used, in certain embodiments, which may be less than about 40 weight percent, or about 20 weight percent of cellulosic material, as compared to the weight of absorbent core.

According to certain embodiments, the basis weight of absorbent particulate polymer material 66 and 74 in at least one freely selected first square measuring 1 cm×1 cm in a zone of greater absorbent particulate polymer material basis weight may be at least 10%, or 20%, or 30%, 40% or 50% higher than the basis weight of absorbent particulate polymer material 66 and 74 in at least one freely selected second square measuring 1 cm×1 cm in a zone of lesser absorbent particulate polymer material basis weight. In a certain embodiment, the first and the second square are centered about the longitudinal axis.

According to an embodiment, a suitable absorbent particulate polymer material 66 and 74, even in the swollen state, i.e., when liquid has been absorbed, does not substantially obstruct the liquid flow throughout the material, especially when the material has a permeability, as expressed by the saline flow conductivity of the absorbent polymer material, of greater than about 10, 40, 80, 100, 110, 120, 150, or $200 \times 10^{-7}$ cm$^3$·sec/g and a centrifuge retention capacity (CRC) of greater than about 20 g/g, greater than about 25 g/g, or less than about 40 g/g, less than about 35 g/g. Saline flow conductivity is a parameter well recognized in the art and is to be measured in accordance with the test disclosed in U.S. Patent Application Publication No. 2007/0219521. Centrifuge retention capacity is another parameter well recognized in the art and is to be measured in accordance with the test disclosed hereinbelow. According to a certain embodiment, the absorbent polymer material has an Absorption Against Pressure (AAP) of at least about 20 g/g, greater than about 23 g/g, or greater than about 25 g/g as measured according to the test described below. Absorbent polymer materials for use in certain embodiments have a basis weight of at least about 200 g/m$^2$, at least about 400 g/m$^2$, or at least about 600 g/m$^2$. To maintain flexibility the basis weight is desirably less than about 2000 g/m$^2$.

In certain embodiments wherein the absorbent core 14 (or 214) is substantially cellulose free, the absorbent core 14 (or 214) has a density greater than about 0.4 g/m$^3$, greater than about 0.5 g/m$^3$, or greater than about 0.6 g/m$^3$.

According to an embodiment, the absorbent particulate polymer material 66 and 74 may be present in the diaper 10 so as to impart an average basis weight of more than about 50, 100, 200, 300, 400, 500, 600, 700, 800 or 900 g/m$^2$. The diaper 10 (or 302), according to an exemplary embodiment, may have a relatively narrow crotch width for increased wearing comfort. The diaper 10 (or 302) may have a crotch width of less than about 100 mm, 90 mm, 80 mm, 70 mm, 60 mm or even less than about 50 mm. Hence, the absorbent core 14 (or 214), according to an embodiment, may have a crotch width as measured along a transversal line which is positioned at equal distance to the front edge and the rear edge of the core which is less than about 100 mm, 90 mm, 80 mm, 70 mm, 60 mm or even less than about 50 mm, as measured along a transversal line which is positioned at equal distance to the front edge and the rear edge of the core. It has been found that, for most absorbent articles such as diapers, the liquid discharge occurs predominately in the front half of the diaper. The front half of the absorbent core 14 may therefore comprise most of the absorbent capacity of the core. Thus, according to certain embodiments, the front half of said absorbent core 14 (or 214) may comprise more than about 60% of the absorbent capacity, or more than about 65%, 70%, 75%, 80%, 85%, or 90% of the absorbent capacity.

In certain embodiments, the absorbent core 14 (or 214) may further comprise any absorbent material that is generally compressible, conformable, non-irritating to the wearer's skin, and capable of absorbing and retaining liquids such as urine and other certain body exudates. In such embodiments, the absorbent core 14 (or 214) may comprise a wide variety of liquid-absorbent materials commonly used in disposable diapers and other absorbent articles such as comminuted wood pulp, which is generally referred to as airfelt, creped cellulose wadding, melt blown polymers, including co-form, chemically stiffened, modified or cross-linked cellulosic fibers, tissue, including tissue wraps and tissue laminates, absorbent foams, absorbent sponges, or any other known absorbent material or combinations of materials. The absorbent core 14 (or 214) may further comprise minor amounts (typically less than 10%) of non-liquid absorbent materials, such as adhesives, waxes, oils and the like.

Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.).

In a certain embodiment best illustrated in FIG. 2, the elasticized leg cuffs 24 may comprise absorbent particulate polymer material 66 which may be laid down directly of the elasticized legs cuffs 24 in the same manner as the absorbent particulate polymer material 66 is laid down on first substrate 64 (described below) or may be formed on a separate substrate and added later.

The thermoplastic material 68 and 76 may serve to cover and at least partially immobilize the absorbent particulate polymer material 66 and 74. In one embodiment of the present invention, the thermoplastic material 68 and 76 can be disposed essentially uniformly within the absorbent particulate polymer material 66 and 74. However, in a certain embodiment, the thermoplastic material 68 and 76 may be provided as a fibrous layer which is at least partially in contact with the absorbent particulate polymer material 66 and 74 and partially in contact with the substrate layers 64 and 72 of the first and second absorbent layers 60 and 62. FIGS. 3, 4, and 7 show such a structure, and in that structure, the absorbent particulate polymer material 66 and 74 is provided as a discontinuous layer, and a layer of fibrous thermoplastic material 68 and 76 is laid down onto the layer of absorbent particulate polymer material 66 and 74, such that the thermoplastic material 68 and 76 is in direct contact with the absorbent particulate polymer material 66 and 74, but also in direct contact with the second surfaces 80 and 84 of the substrates 64 and 72, where the substrates are not covered by the absorbent particulate polymer material 66 and 74. This imparts an essentially three-dimensional structure to the fibrous layer of thermoplastic material 68 and 76, which in itself is essentially a two-dimensional structure of relatively small thickness, as compared to the extension in length and width directions. In other words, the thermoplastic material 68 and 76 undulates between the absorbent particulate polymer material 68 and 76 and the second surfaces of the substrates 64 and 72.

Thereby, the thermoplastic material 68 and 76 may provide cavities to cover the absorbent particulate polymer material 66 and 74, and thereby immobilizes this material. In a further aspect, the thermoplastic material 68 and 76 bonds to the substrates 64 and 72 and thus affixes the absorbent particulate polymer material 66 and 74 to the substrates 64 and 72. Thus, in accordance with certain embodiments, the thermoplastic material 68 and 76 immobilizes the absorbent particulate polymer material 66 and 74 when wet, such that the absorbent core 14 achieves a wet immobilization of more than about 50%, or more than about 60%, 70%, 80% or 90% according to the Wet Immobilization Test. The Wet Immobilization Test is described in U.S. Patent Application Publication No. 2004/0162536, the disclosure of which is expressly incorporated herein by reference. Some thermoplastic materials will also penetrate into both the absorbent particulate polymer material 66 and 74 and the substrates 64 and 72, thus providing for further immobilization and affixation. According to certain embodiments, the thermoplastic material 68 and 76 may have an effective mesh size less than 300 microns.

Of course, while the thermoplastic materials disclosed herein provide a much improved wet immobilization (i.e., immobilization of absorbent material when the article is wet or at least partially loaded), these thermoplastic materials may also provide a very good immobilization of absorbent material when the absorbent core 14 (or 214) is dry.

According to certain embodiments, the thermoplastic material 68 and 76 can comprise any thermoplastic material, including, but not limited to adhesive thermoplastic materials, also referred to as hot melt adhesives. Some initially thermoplastic materials may later lose their thermoplasticity due to a curing step, e.g., initiated via heat, UV radiation, electron beam exposure or moisture or other means of curing, leading to the irreversible formation of a crosslinked network of covalent bonds. Those materials having lost their initial thermoplastic behavior are herein also understood as thermoplastic materials.

Without wishing to be bound by theory, it has been found that those thermoplastic materials which are most useful for immobilizing the absorbent particulate polymer material 66 and 74 combine good cohesion and good adhesion behavior. Good adhesion may promote good contact between the thermoplastic material 68 and 76 and the absorbent particulate polymer material 66 and 74 and the substrates 64 and 72. Good cohesion reduces the likelihood that the adhesive breaks, in particular in response to external forces, and namely in response to strain. When the absorbent core 14 (or 214) absorbs liquid, the absorbent particulate polymer material 66 and 74 swells and subjects the thermoplastic material 68 and 76 to external forces. In certain embodiments, the thermoplastic material 68 and 76 may allow for such swelling, without breaking and without imparting too many compressive forces, which would restrain the absorbent particulate polymer material 66 and 74 from swelling.

In accordance with certain embodiments, the thermoplastic material 68 and 76 may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic material may be a hot melt adhesive comprising at least one thermoplastic polymer in combination with other thermoplastic diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or $0°$ C.$<T_g<20°$ C. In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alphaolefins.

In exemplary embodiments, the resin has typically a Mw below 5,000 and a Tg usually above room temperature, typical concentrations of the resin in a hot melt are in the range of about 30 to about 60%, and the plasticizer has a low Mw of typically less than 1,000 and a Tg below room temperature, with a typical concentration of 0-15%.

In certain embodiments, the thermoplastic material 68 and 76 is present in the form of fibers. In some embodiments, the fibers will have an average thickness of about 1 to about 50 micrometers or about 1 to about 35 micrometers and an average length of about 5 mm to about 50 mm or about 5 mm to about 30 mm. To improve the adhesion of the thermoplastic material 68 and 76 to the substrates 64 and 72 or to any other layer, in particular any other non-woven layer, such layers may be pre-treated with an auxiliary adhesive.

In certain embodiments, the thermoplastic material 68 and 76 will meet at least one, or several, or all of the following parameters:

An exemplary thermoplastic material 68 and 76 may have a storage modulus G' measured at 20° C. of at least 30,000 Pa and less than 300,000 Pa, or less than 200,000 Pa, or between 140,000 Pa and 200,000 Pa, or less than 100,000 Pa. The storage modulus G' at 20° C. may be a measure for the permanent "tackiness" or permanent adhesion of the thermoplastic material used. In a further aspect, the storage modulus G' measured at 35° C. may be greater than 100,000 Pa. In a further aspect, the storage modulus G' measured at 60° C. may be less than 300,000 Pa and more than 18,000 Pa, or more than 24,000 Pa, or more than 30,000 Pa, or more than 90,000 Pa. The storage modulus measured at 60° C. may be a measure for the form stability of the thermoplastic material at elevated ambient temperatures. This value is particularly important if the absorbent product is used in a hot climate where the thermoplastic material would lose its integrity if the storage modulus G' at 60° C. is not sufficiently high.

G' is typically measured using a rheometer as schematically shown in FIG. 11 for the purpose of general illustration only. The rheometer 127 is capable of applying a shear stress to the adhesive and measuring the resulting strain (shear deformation) response at constant temperature. The adhesive is placed between a Peltier-element acting as lower, fixed plate 128 and an upper plate 129 with a radius R of e.g., 10 mm, which is connected to the drive shaft of a motor to generate the shear stress. The gap between both plates has a height H of e.g., 1500 micron. The Peltier-element enables to control the temperature of the material (+0.5° C.).

In a further embodiment, the thermoplastic material 68 and 76 may have a deformation resistance strain in % between about 20 and about 90.

In a further aspect, the loss angle tan Delta of the adhesive at 60° C. may be below the value of 2, or below the value of 1, or below the value of 0.5. The loss angle tan Delta at 60° C. is correlated with the liquid character of an adhesive at elevated ambient temperatures. The lower tan Delta, the more an adhesive behaves like a solid rather than a liquid, i.e., the lower its tendency to flow or to migrate and the lower the tendency of an adhesive superstructure as described herein to deteriorate or even to collapse over time. This value is hence particularly important if the absorbent article is used in a hot climate.

In a further embodiment, the thermoplastic material 68 and 76 may have a glass transition temperature $T_g$ of less than 25° C., or less than 22° C., or less than 18° C., or less than 15° C. A low glass transition temperature $T_g$ is beneficial for good adhesion. In a further embodiment, a low glass transition temperature $T_g$ ensures that the adhesive thermoplastic material does not become too brittle.

In a further embodiment, the thermoplastic material 68 and 76 may have an elasticity factor from about 10 to about 20.

In yet a further embodiment, the thermoplastic material 68 and 76 may have a sufficiently high cross-over temperature. A sufficiently high cross-over temperature $T_x$ has been found beneficial for high temperature stability of the thermoplastic layer and hence it ensures good performance of the absorbent product and in particular good wet immobilization even under conditions of hot climates and high temperatures. Therefore, $T_x$ may be above 80° C., or above 85° C., above 90° C., or above 95° C.

As described hereinabove, the absorbent core 14 (or 214) may also comprise an auxiliary adhesive layer 69. The auxiliary adhesive may be deposited on the first and second substrates 64 and 72 of the respective first and second absorbent layers 60 and 62 before application of the absorbent particulate polymer material 66 and 74 for enhancing adhesion of the absorbent particulate polymer materials 66 and 74 and the thermoplastic material 68 and 76 to the respective substrates 64 and 72. The auxiliary glue 69 may also aid in immobilizing the absorbent particulate polymer material 66 and 74 and may comprise the same thermoplastic material as described hereinabove or may also comprise other adhesives including but not limited to sprayable hot melt adhesives, such as H.B. Fuller Co. (St. Paul, MN) Product No. HL-1620-B. The auxiliary glue may be applied to the substrates 64 and 72 by any suitable means, but according to certain embodiments, may be applied in about 0.5 to about 1 mm wide slots spaced about 0.5 to about 2 mm apart.

The cover layer 70 shown in FIG. 4 may comprise the same material as the substrates 64 and 72, or may comprise a different material. In certain embodiments, suitable materials for the cover layer 70 are the non-woven materials, typically the materials described above as useful for the substrates 64 and 72.

In a certain embodiment not illustrated, the absorbent core 14 (or 214) may be wrapped by a core wrap material. In one embodiment, the core wrap material comprises a top layer and a bottom layer. The core wrap material, the top layer or the bottom layer may be provided from a non-woven material. Such a core wrap may be provided from two or more separate sheets of materials or they may be alternatively provided from a unitary sheet of material. A unitary sheet of material may be wrapped around the storage layer 60, e.g., in a C-fold.

In a certain embodiment, the absorbent core 214 is substantially cellulose free. In this embodiment, the cavity 215 advantageously provides a void volume for the fecal matter even when the absorbent core is already liquid, e.g., urine) loaded. Moreover, it provides bowel movement distribution toward the back of the diaper, away from the wearer's genitals, providing easier clean up. In an embodiment with an elasticized top sheet 311, the cavity 215 advantageously works as a space between the absorbent core 214 and the elasticized top sheet 311, so that the bowel movement is directed underneath the top sheet. In addition, in an embodiment where there is little or no absorbent particulate polymer material at the bottom of the cavity, when a bowel movement gets into the cavity, it becomes visible from the outside through the back sheet. This advantageously may serve as a positive signaling function for the caretaker of the wearer to check/change the diaper or training pant.

In one embodiment, the visibility of the at least one cavity 215 is enhanced by the inclusion of a color, print, pattern, or a combination thereof, in one or more layers of the absorbent article. For example, in one case, the cavity may be made more visible by including a colored (i.e., non-white) layer below the cavity, such that the color can be seen in the cavity due to the lower (or zero) basis weight in that region of the absorbent core. In another embodiment, a colored layer may be added over top of the cavity, e.g., the core cover, top sheet, or as a new, additional layer.

Method and Apparatus for Making Absorbent Articles

Figure 16:
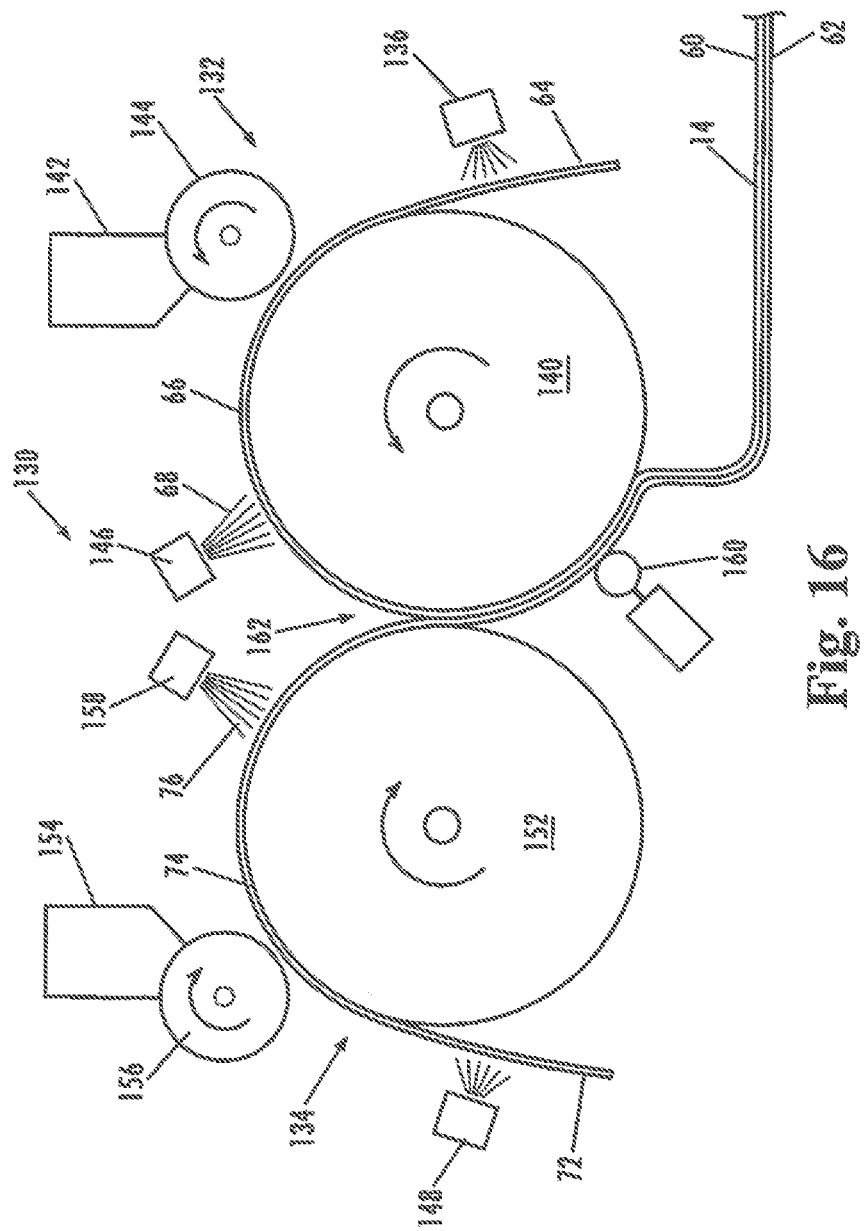
FIG. 16 is a schematic illustration of a process for making an absorbent core in accordance with an embodiment of this invention.

A printing system 130 for making an absorbent core 14 in accordance with an embodiment of this invention is illustrated in FIG. 16 and may generally comprise a first printing unit 132 for forming the first absorbent layer 60 of the absorbent core 14 and a second printing unit 134 for forming the second absorbent layer 62 of the absorbent core 14. It is understood throughout the following description that this system would be equally applicable to the making of absorbent core 214.

The first printing unit 132 may comprise a first auxiliary adhesive applicator 136 for applying an auxiliary adhesive 69 to the substrate 64, which may be a nonwoven web, a first rotatable support roll 140 for receiving the substrate 64, a hopper 142 for holding absorbent particulate polymer material 66, a printing roll 144 for transferring the absorbent particulate polymer material 66 to the substrate 64, and a thermoplastic material applicator 146 for applying the thermoplastic material 68 to the substrate 64 and the absorbent particulate polymer 66 material thereon.

The second printing unit 134 may comprise a second auxiliary adhesive applicator 148 for applying an auxiliary adhesive 73 to the second substrate 72, a second rotatable support roll 152 for receiving the second substrate 72, a second hopper 154 for holding the absorbent particulate polymer material 74, a second printing roll 156 for transferring the absorbent particulate polymer material 74 from the hopper 154 to the second substrate 72, and a second thermoplastic material applicator 158 for applying the thermoplastic material 76 to the second substrate 72 and the absorbent particulate polymer material 74 thereon.

The printing system 130 also includes a guide roller 160 for guiding the formed absorbent core from a nip 162 between the first and second rotatable support rolls 140 and 152.

The first and second auxiliary applicators 136 and 148 and the first and second thermoplastic material applicators 146 and 158 may be a nozzle system which can provide a relatively thin but wide curtain of thermoplastic material.

Figure 17:
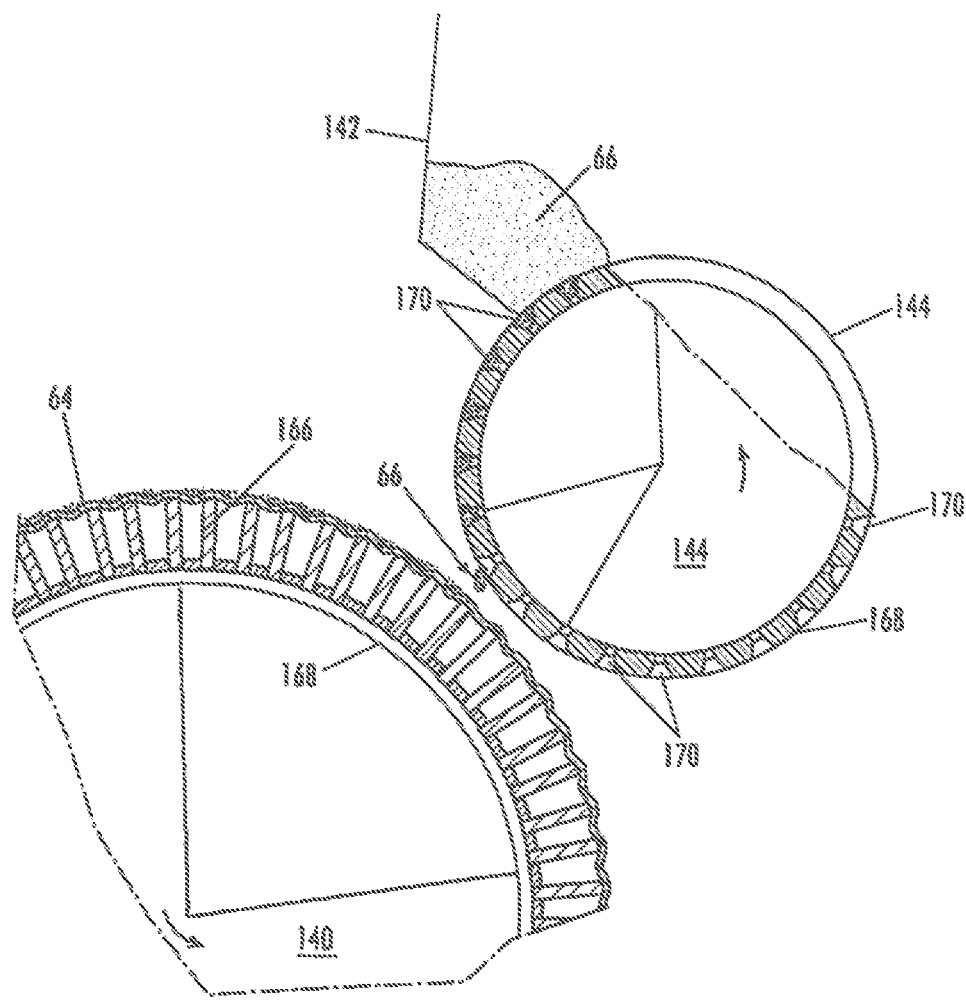
FIG. 17 is a partial sectional view of an apparatus for making an absorbent core in accordance with an embodiment of this invention.
Figure 20:
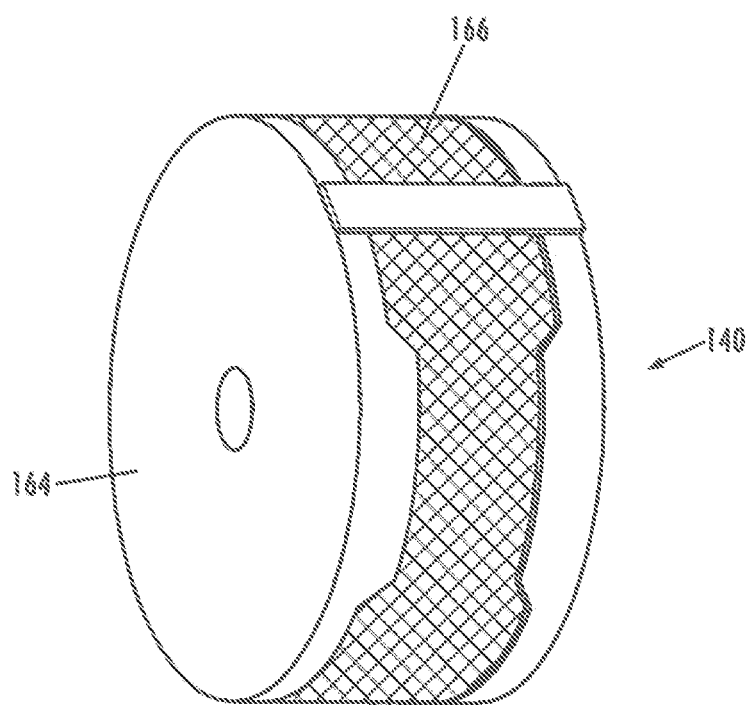
FIG. 20 is a perspective view of the supporting roll illustrated in FIG. 16.

Turning to FIG. 17, portions of the first hopper 142, first support roll 140, and first printing roll 144 are illustrated. As also shown in FIG. 20, the first rotatable support roll 140, which has the same structure as the second rotatable support roll 152, comprises a rotatable drum 164 and a peripheral vented support grid 166 for receiving the first substrate 64.

Figure 18:
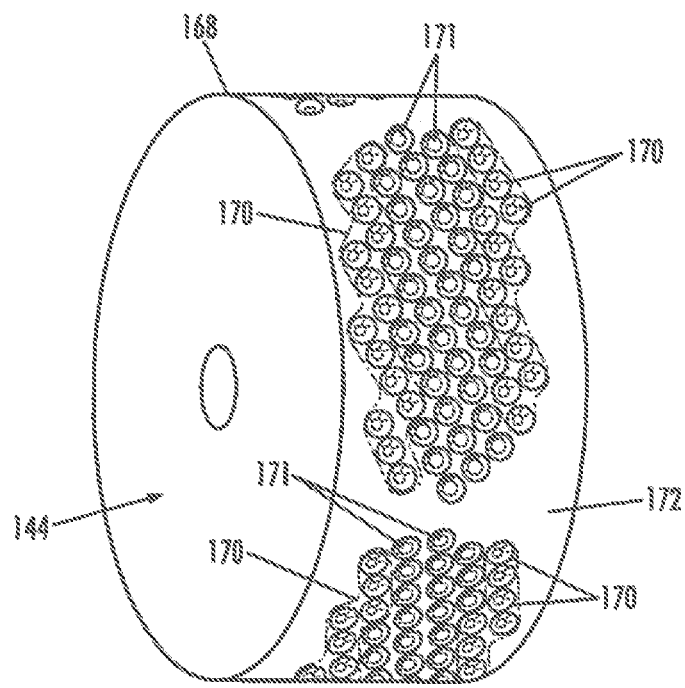
FIG. 18 is a perspective view of the printing roll illustrated in FIG. 17.

As also illustrated in FIG. 18, the first printing roll 144, which has the same structure as the second printing roll 156, comprises a rotatable drum 168 and a plurality of absorbent particulate polymer material reservoirs 170 and 171 in a peripheral surface 172 of the drum 168. The reservoirs 170 and 171, best illustrated in FIG. 19, may have a variety of shapes, including cylindrical, conical, or any other shape. The reservoirs 170 and 171 may lead to an air passage 174 in the drum 168 and comprise a vented cover 176 for holding adhesive particulate polymer material 66 in the reservoir and preventing the adhesive particulate polymer material 66 from falling or being pulled into the air passage 174.

Figure 5:
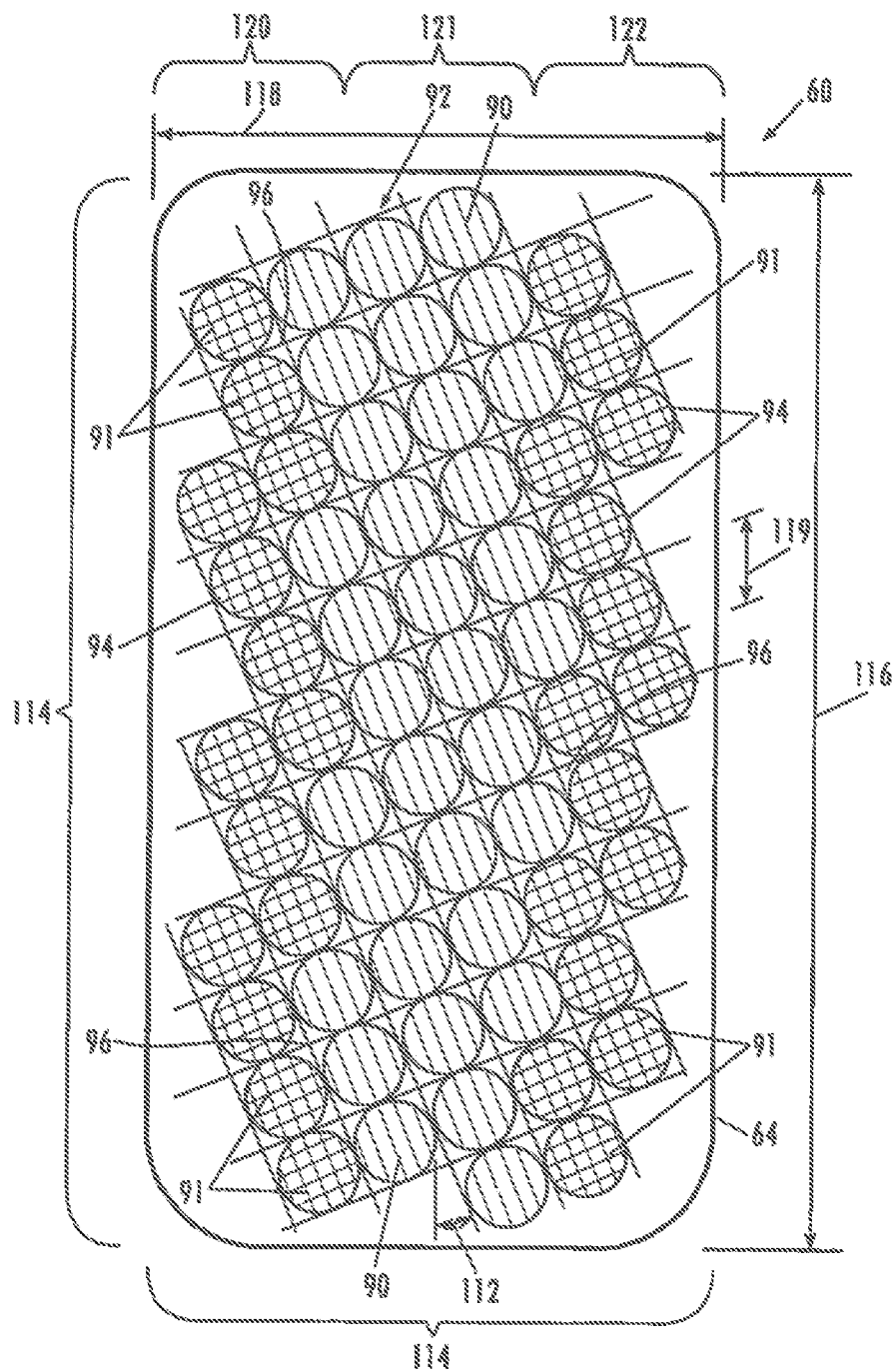
FIG. 5 is a plan view of the absorbent core layer illustrated in FIG. 3.
Figure 19:
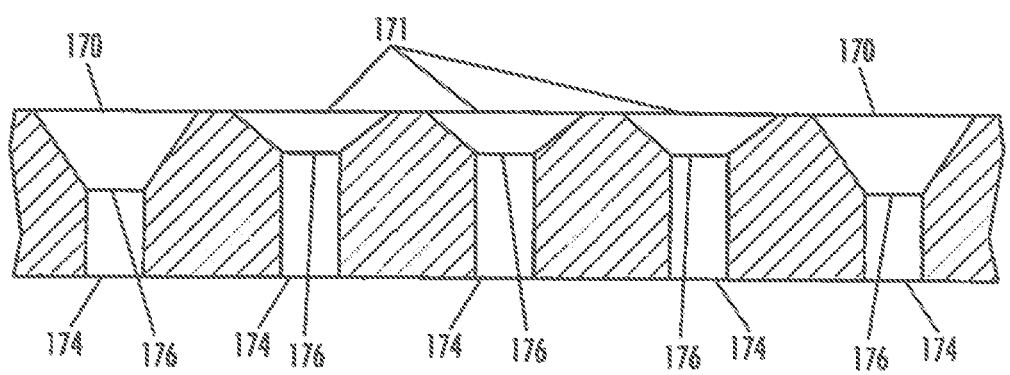
FIG. 19 is a partial sectional view of the printing roll illustrated in FIG. 18 showing absorbent particulate polymer material reservoirs.

The first printing roll 144 is designed to produce a certain embodiment like the absorbent core 14 illustrated in FIG. 5 wherein side absorbent zones 120 and 122 have a higher basis weight of absorbing particulate polymer material 66 and 74 than the central absorbent zone 121. In the embodiment illustrated in FIG. 19, this effect may be achieved by having a corresponding set of reservoirs 170 which are relatively deep and a second set 171 of reservoirs which are relatively shallow, such that the deeper reservoirs 170 carry more absorbent particulate polymer material and deliver more absorbent particulate polymer material 66 to the side absorbent zones 120 and 122 and the more shallow reservoirs 171 hold less adhesive particulate polymer material and deliver less absorbent particulate polymer material 66 to the central zone 121 of the absorbent core 14. The sets of deeper and shallower reservoirs 170 and 171, of course, can be arranged in any variety of patterns to define the cavity 215 of absorbent core 214, as well as in configurations to create an absorbent core with any corresponding variety of varying absorbent particulate polymer material basis weights across the absorbent core 214. FIG. 19, in particular, illustrates the difference in volumetric sizes of first and second sets of reservoirs 170 and 171.

Other methods of forming the cavity and delivering a varying profile of absorbent particulate polymer basis weights to the absorbent core 14 or 214 include, but are not limited to, applying a higher vacuum in sections of the first and second rotatable support rolls 140 and 152 where more absorbent particulate polymer material is desired or, when the absorbent particulate polymer material is delivered to the absorbent core substrate 64 pneumatically, such as when combining cellulosic fibers with absorbent particulate polymer material, directing the air stream carrying the absorbent particulate polymer material and cellulosic fibers to areas of the absorbent core substrate where a higher basis weight of absorbent particulate polymer material is desired.

Figure 6:
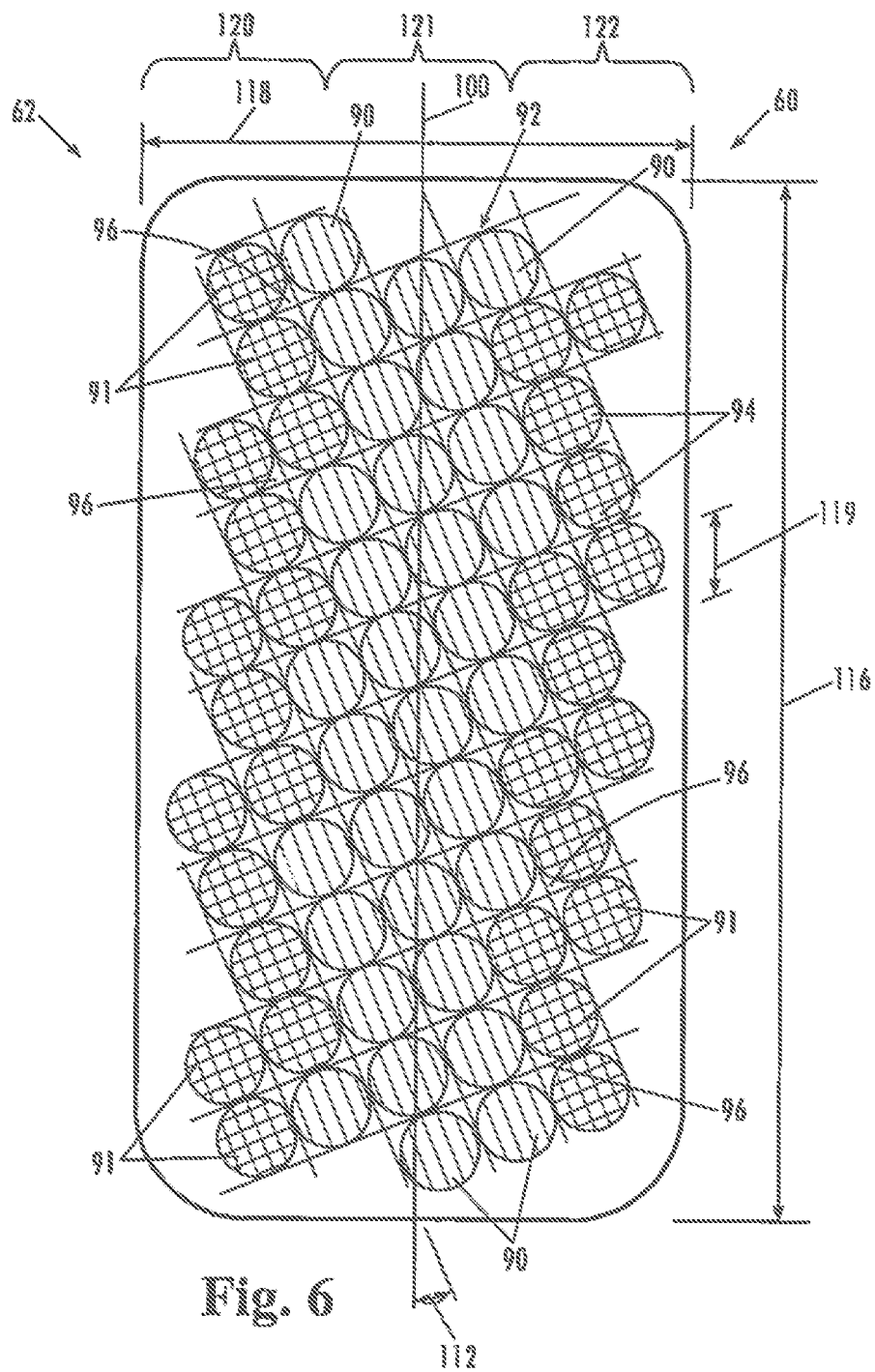
FIG. 6 is a plan view of a second absorbent core layer in accordance with an embodiment of this invention wherein more absorbent particulate polymer material is present toward lateral edges of the diaper than in a central zone of the diaper.

In operation, the printing system 130 receives the first and second substrate 64 and 72 into the first and second printing units 132 and 134, respectively, the first substrate 64 is drawn by the rotating first support roll 140 past the first auxiliary adhesive applicator 136 which applies the first auxiliary adhesive to the first substrate 64 in a pattern such as described hereinabove. A vacuum (not shown) within the first support roll 140 draws the first substrate 64 against the vertical support grid 166 and holds the first substrate 64 against the first support roll 140. This presents an uneven surface on the first substrate 64. Due to gravity, or by using the vacuum means, the substrate 64 will follow the contours of the uneven surface and thereby the substrate 64 will assume a mountain and valley shape. The absorbent particulate polymer material 66 may accumulate in the valleys presented by the substrate 64. The first support roll 140 then carries the first substrate 64 past the rotating first printing roll 144 which transfers the absorbent particulate polymer material 66 from the first hopper 142 to the first substrate 64 in the grid pattern 92 which is best illustrated in FIGS. 5 and 6. A vacuum (not shown) in the first printing roll 144 may hold the absorbent particulate polymer material 66 in the reservoirs 170 until time to deliver the absorbent particulate polymer material 66 to the first substrate 64. The vacuum may then be released or air flow through the air passages 174 may be reversed to eject the absorbent particulate polymer material 66 from the reservoirs and onto the first substrate 64. The absorbent particulate polymer material 66 may accumulate in the valleys presented by the substrate 64. The support roll 140 then carries the printed first substrate 64 past the thermoplastic material applicator 136 which applies the thermoplastic material 68 to cover the absorbent particulate polymer material 66 on the first substrate 64.

Hence, the uneven surface of the vented support grid 166 of the support rolls 140 and 152 determines the distribution of absorbent particulate polymeric material 66 and 74 throughout the absorbent core 14 and likewise determines the pattern of junction areas 96.

Meanwhile, the second rotatable support roll draws the second substrate 72 past the second auxiliary adhesive applicator 148 which applies an auxiliary adhesive to the second substrate 72 in a pattern such as is described hereinabove. The second rotatable support roll 152 then carries the second substrate 72 past the second printing roll 156 which transfers the absorbent particulate polymer material 74 from the second hopper 154 to the second substrate 72 and deposits the absorbent particulate polymer material 74 in the grid pattern 92 on the second substrate 72 in the same manner as described with regard to the first printing unit 132 above. The second thermoplastic material applicator 158 then applies the thermoplastic material 76 to cover the absorbent particulate polymer material 74 on the second substrate 72. The printed first and second substrates 64 and 72 then pass through the nip 162 between the first and second support rolls 140 and 152 for compressing the first absorbent layer 60 and second absorbent layer 62 together to form the absorbent core 14.

In an optional further process step a cover layer 70 may be placed upon the substrates 64 and 72, the absorbent particulate polymer material 66 and 74, and the thermoplastic material 68 and 76. In another embodiment, the cover layer 70 and the respective substrate 64 and 72 may be provided from a unitary sheet of material. The placing of the cover layer 70 onto the respective substrate 64 and 72 may then involve the folding of the unitary piece of material.

Figure 21:
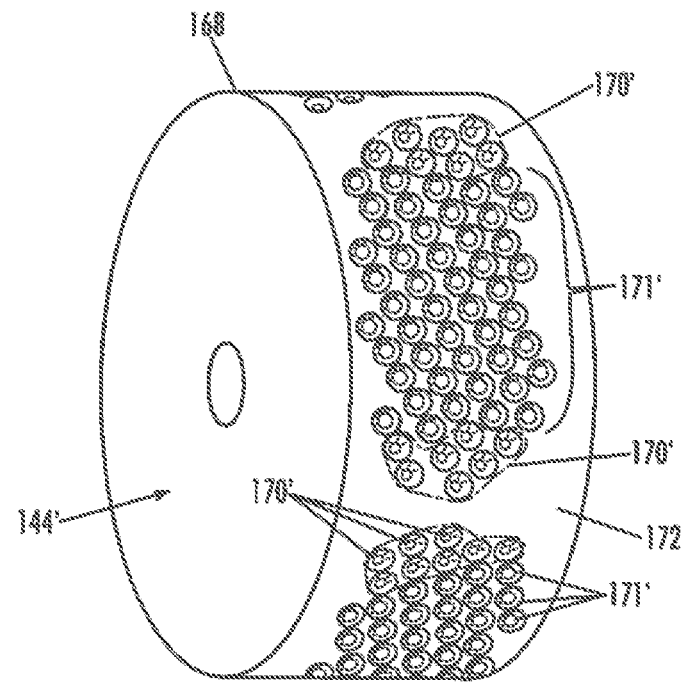
FIG. 21 is a perspective view of a printing roll for making an absorbent core wherein more absorbent particulate polymer material is present toward ends of the diaper than in a central zone of the diaper.
Figure 22:
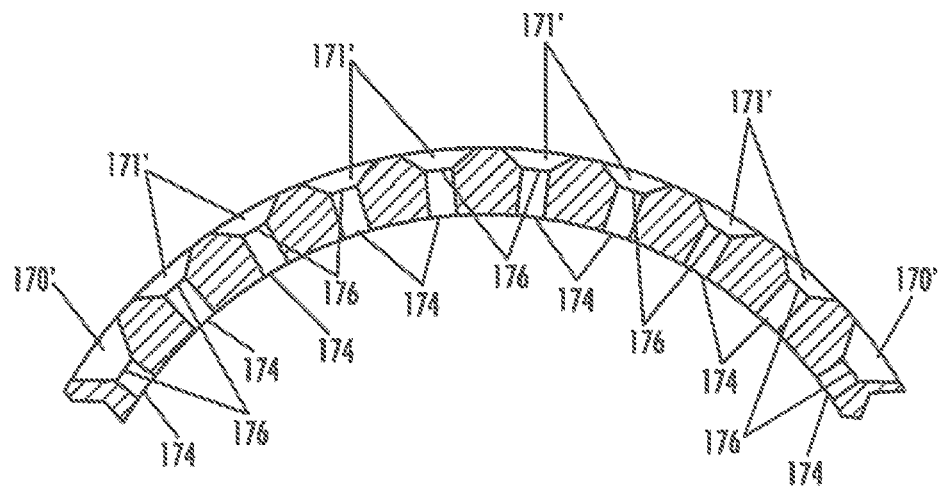
FIG. 22 is a partial sectional view of the printing roll illustrated in FIG. 21 showing absorbent particulate polymer material reservoirs.
Figure 23:
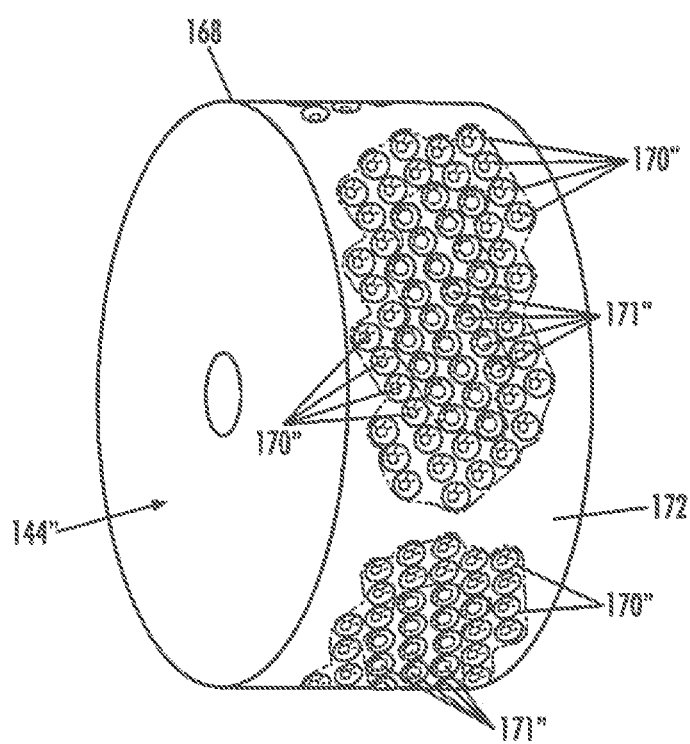
FIG. 23 is a perspective view of a printing roll for making an absorbent wherein more absorbent particulate polymer material is present toward lateral edges and ends of the diaper than in a central zone of the diaper.

FIGS. 21-23 illustrate certain embodiments of printing rolls 144' and 144" for making corresponding embodiments of absorbent cores 14' and 14" illustrated in FIGS. 9 and 10, respectively. As shown in FIGS. 21 and 22, the printing roll 144' for making the absorbent core 14' illustrated in FIG. 9 comprises sets of deeper and shallower reservoirs 170' and 171' for forming the end absorbent zones 123 and 124, which have a higher absorbent particulate polymer material basis weight, and the central absorbent zone 125, which has a lower absorbent particulate polymer material basis weight, respectively. Likewise, the printing roll 144" has sets of deeper and shallower reservoirs 170" and 171", respectively, for forming the side absorbent zones 120' and 122' and end absorbent zones 123' and 124', having a higher basis weight of absorbent particulate polymer material, and the central zone 121' and 125' having a lower basis weight of absorbent particulate polymer material. This technique of profiling the absorbent particulate polymer material in both the MD and CD may be readily adapted to form a cavity, defined at least in part by the lower basis weight of absorbent particulate polymer material in an elongated central region.

Absorbent articles such as the diapers 10 made in accordance with embodiments of this invention may be folded and packaged for distribution and sale. Absorbent articles are typically bi-folded, but may also be tri-folded. After folding, the folded absorbent articles may be stacked to form a stack comprising a plurality of absorbent articles. The stack may then be compressed and encased in a packaging material such as a bag, a pouch, a box, or the like.

All patents and patent applications (including any patents which issue thereon) assigned to the Procter & Gamble Company referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
    a. a topsheet;
    b. a backsheet;
    c. an absorbent core disposed between the topsheet and the backsheet, the absorbent core comprising a first substrate, a second substrate, and absorbent particulate polymer material and wood pulp arranged between the first substrate and the second substrate; and
    d. an acquisition layer disposed between the absorbent core and the topsheet;
    e. wherein the absorbent core comprises a longitudinally-extending cavity comprising a cavity volume;
    f. wherein the second substrate deflects into the cavity and is adhered to the first substrate within the cavity;
    g. wherein the cavity volume increases when the absorbent particulate polymer material is contacted with a liquid and swells;
    h. wherein the second substrate is adhered to the first substrate within the cavity via glue; and
    i. wherein the cavity does not reach any longitudinal or lateral edge of the absorbent core.

2. The absorbent article of claim 1, wherein the cavity has a perimeter at least partially defined by the absorbent particulate polymer material.

3. The absorbent article of claim 1, wherein the cavity is substantially free of the absorbent particulate polymer material and the wood pulp.

4. The absorbent article of claim 1, wherein the absorbent core exhibits a wet immobilization of more than 50%, according to the Wet Immobilization Test.

5. The absorbent article of claim 1, wherein the absorbent article is a taped diaper.

6. The absorbent article of claim 1, wherein the cavity is located in the absorbent core along a central longitudinal axis of the absorbent article at a position which, when the absorbent article is worn by a wearer, will be in alignment with a predetermined region about an anus of the wearer.

7. The absorbent article of claim 1, further comprising an acquisition system comprising a nonwoven.

8. An absorbent article comprising:
    a. a topsheet;
    b. a backsheet; and
    c. an absorbent core disposed between the topsheet and the backsheet, the absorbent core comprising a first substrate, a second substrate, and absorbent particulate polymer material arranged between the first substrate and the second substrate;
    d. wherein the absorbent core comprises a longitudinally-extending cavity comprising a cavity volume;
    e. wherein the cavity volume increases when the absorbent particulate polymer material is contacted with a liquid and swells;
    f. wherein the second substrate deflects into the cavity and is adhered to the first substrate within the cavity; and
    g. wherein the cavity does not reach any longitudinal or lateral edge of the absorbent core.

9. The absorbent article of claim 8, wherein the cavity is substantially free of absorbent particulate polymer material.

10. The absorbent article of claim 9, wherein the cavity has a perimeter at least partially defined by the absorbent particulate polymer material.

11. The absorbent article of claim 8, wherein the absorbent core further comprises wood pulp.

12. The absorbent article of claim 8, wherein the absorbent core exhibits a wet immobilization of more than 50%, according to the Wet Immobilization Test.

13. The absorbent article of claim 8, wherein the second substrate is adhered to the first substrate within the cavity via glue.

14. The absorbent article of claim 8, wherein the second substrate is adhered to the first substrate within the cavity via heat and/or pressure.

* * * * *